United States Patent [19]
Small et al.

[11] Patent Number: 6,027,643
[45] Date of Patent: Feb. 22, 2000

[54] ION CHROMATOGRAPHIC METHOD AND APPARATUS USING A COMBINED SUPPRESSOR AND ELUENT GENERATOR

[75] Inventors: Hamish Small, Leland, Mich.; John M. Riviello, Santa Cruz; Yan Liu, Santa Clara, both of Calif.; Nebojsa Avdalovic, San Jose, Calif.

[73] Assignee: Dionex Corporation, Sunnyvale, Calif.

[21] Appl. No.: 09/145,120

[22] Filed: Sep. 2, 1998

Related U.S. Application Data

[63] Continuation-in-part of application No. 08/925,813, Sep. 4, 1997, abandoned.

[51] Int. Cl.$^7$ .................................................. B01D 15/08
[52] U.S. Cl. ...................... 210/198.2; 243/635; 243/656; 205/789; 422/70
[58] Field of Search .................................. 210/635, 638, 210/656, 659, 748, 85, 198.2, 243; 422/70; 205/789, 792.5

[56] References Cited

U.S. PATENT DOCUMENTS

| | | | |
|---|---|---|---|
| 3,897,213 | 7/1975 | Stevens et al. | 23/253 |
| 3,920,397 | 11/1975 | Small et al. | 23/230 |
| 3,925,019 | 12/1975 | Small et al. | 23/230 |
| 3,926,559 | 12/1975 | Stevens et al. | 23/230 |
| 4,459,357 | 7/1984 | Jansen | 210/656 |
| 4,751,004 | 6/1988 | Stevens | 210/659 |
| 4,861,555 | 8/1989 | Mowery | 210/198.2 |
| 4,952,126 | 8/1990 | Hanaoka | 210/656 |
| 5,045,204 | 9/1991 | Dasgupta et al. | 210/635 |
| 5,248,426 | 9/1993 | Stillian | 210/659 |
| 5,352,360 | 10/1994 | Stillian | 210/198.2 |
| 5,569,365 | 10/1996 | Rabin | 204/450 |
| 5,597,734 | 1/1997 | Small | 210/656 |
| 5,663,171 | 9/1997 | Small | 210/198.2 |
| 5,759,405 | 6/1998 | Anderson, Jr. et al. | 210/656 |
| 5,773,615 | 6/1998 | Small | 436/161 |
| 5,914,025 | 6/1999 | Small | 205/789 |
| 5,935,443 | 8/1999 | Anderson | 210/198.2 |

*Primary Examiner*—Ernest G. Therkorn
*Attorney, Agent, or Firm*—David J. Brezner; Flehr Hohbach Test Albritton & Herbert LLP

[57] ABSTRACT

Disclosed is a method and apparatus for electrolytically generating an acid or base eluent in an aqueous solution and for simultaneously suppressing conductivity of the eluent in an ion exchange bed after chromatographic separation in an ion chromatography system.

22 Claims, 15 Drawing Sheets

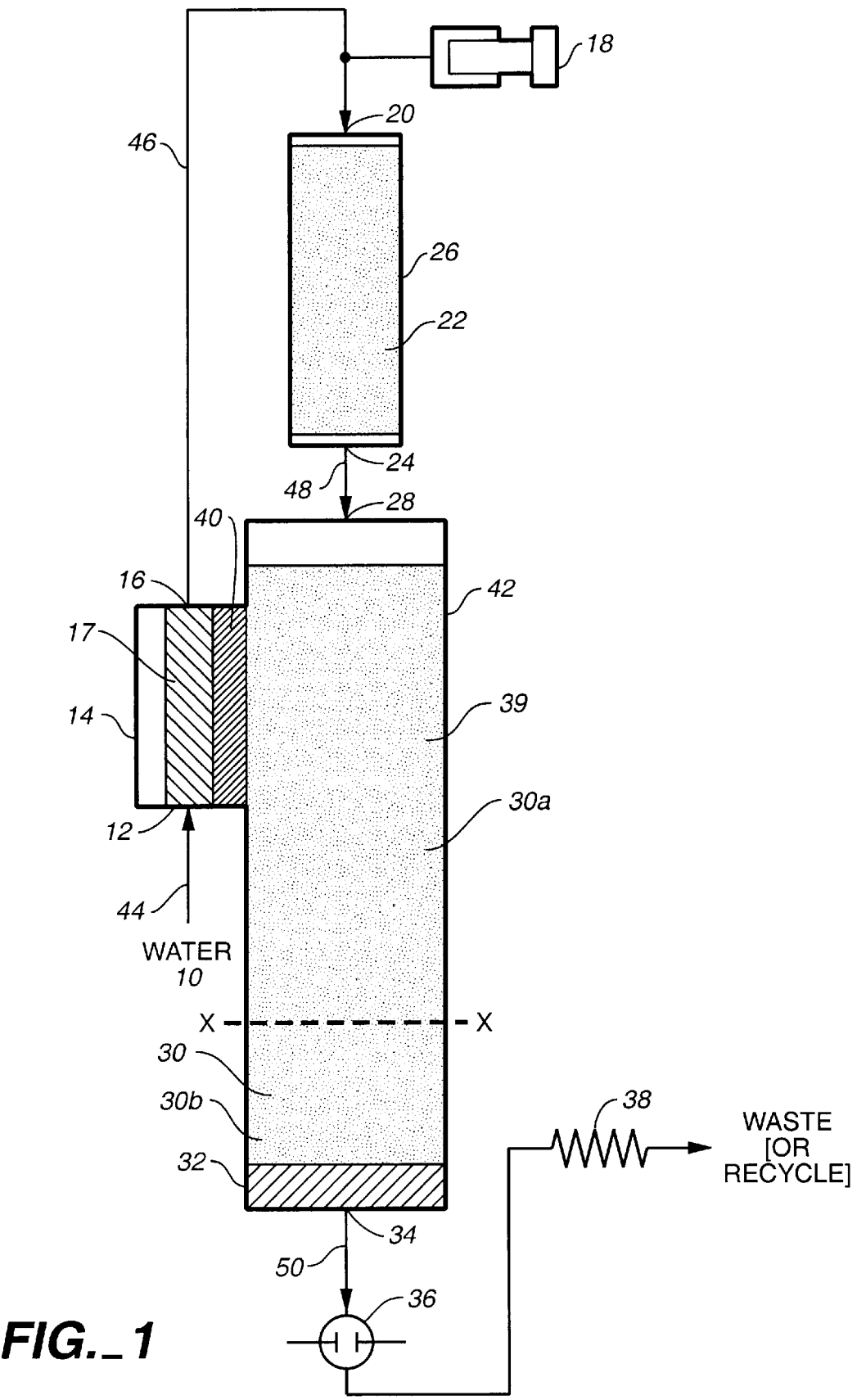
FIG._1

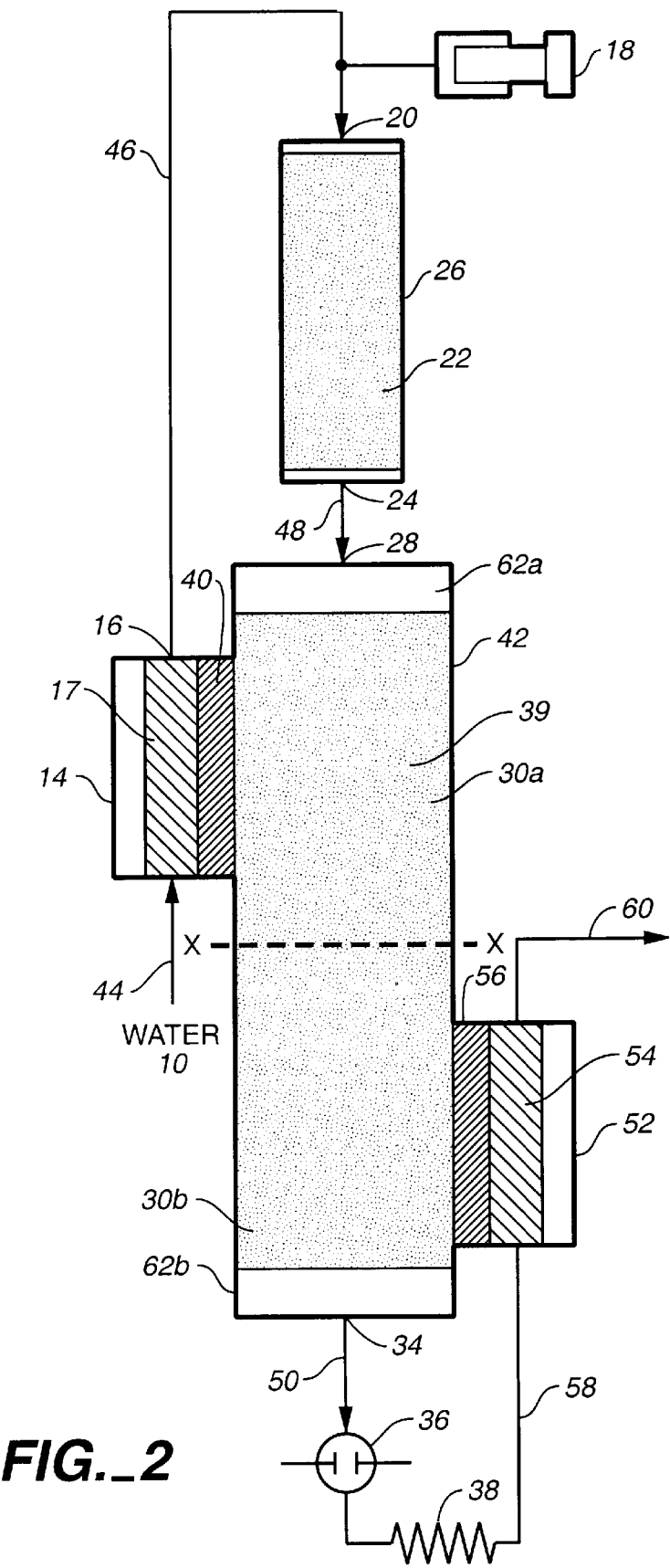
FIG._2

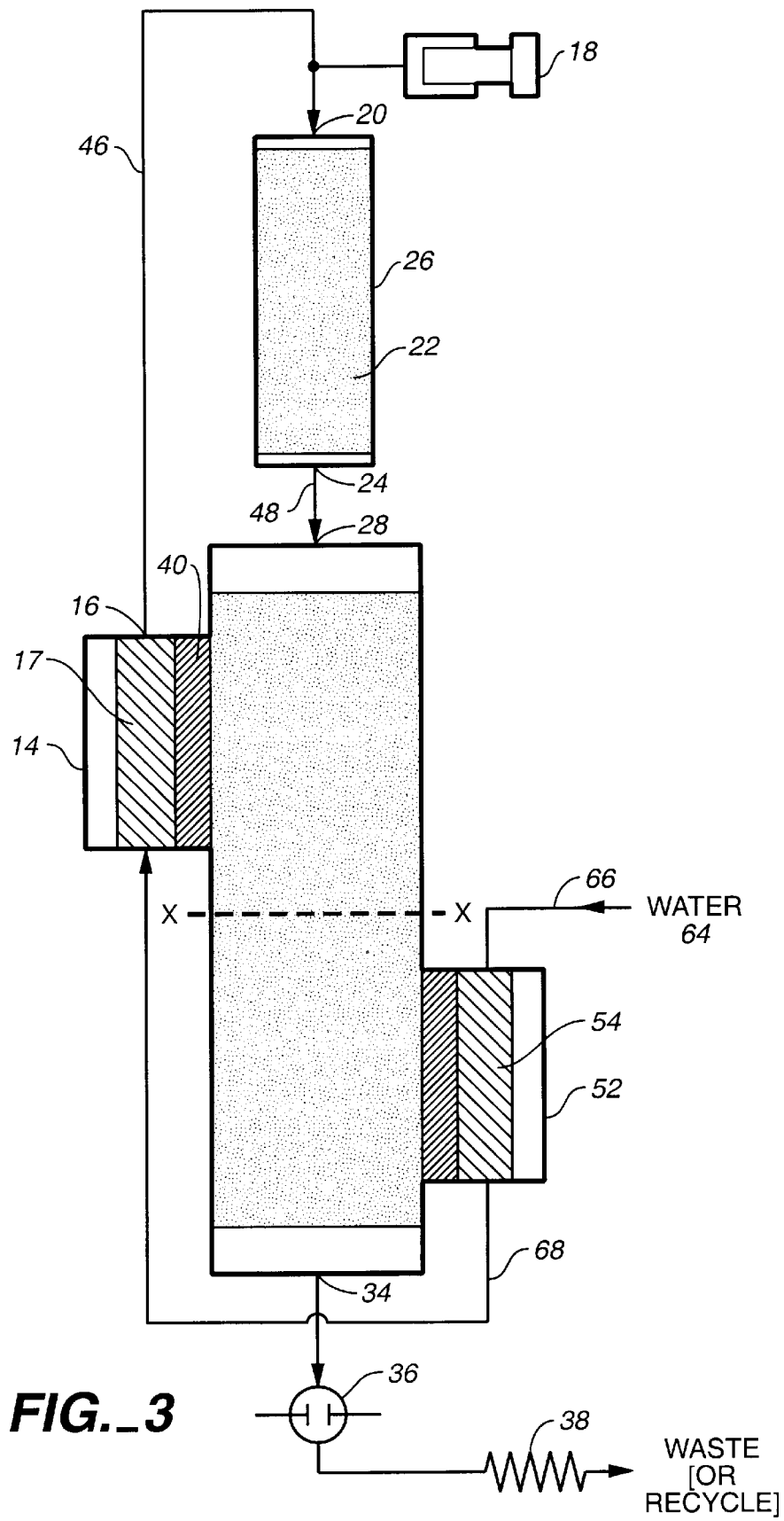
FIG._3

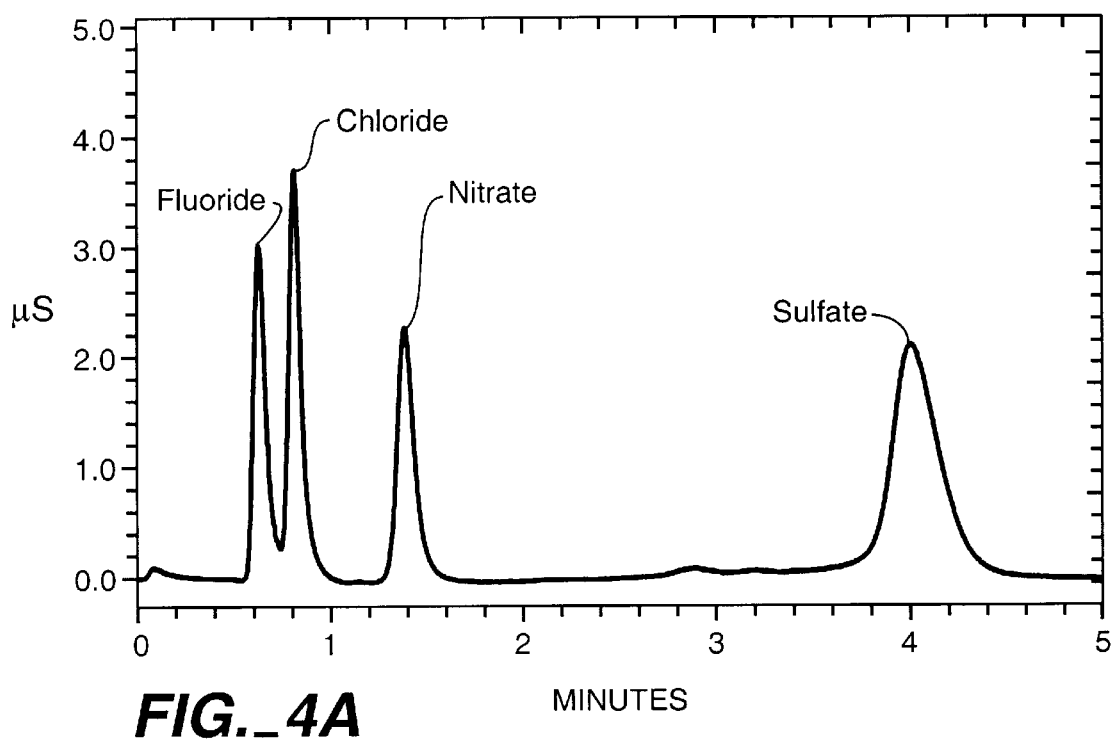
FIG._4A
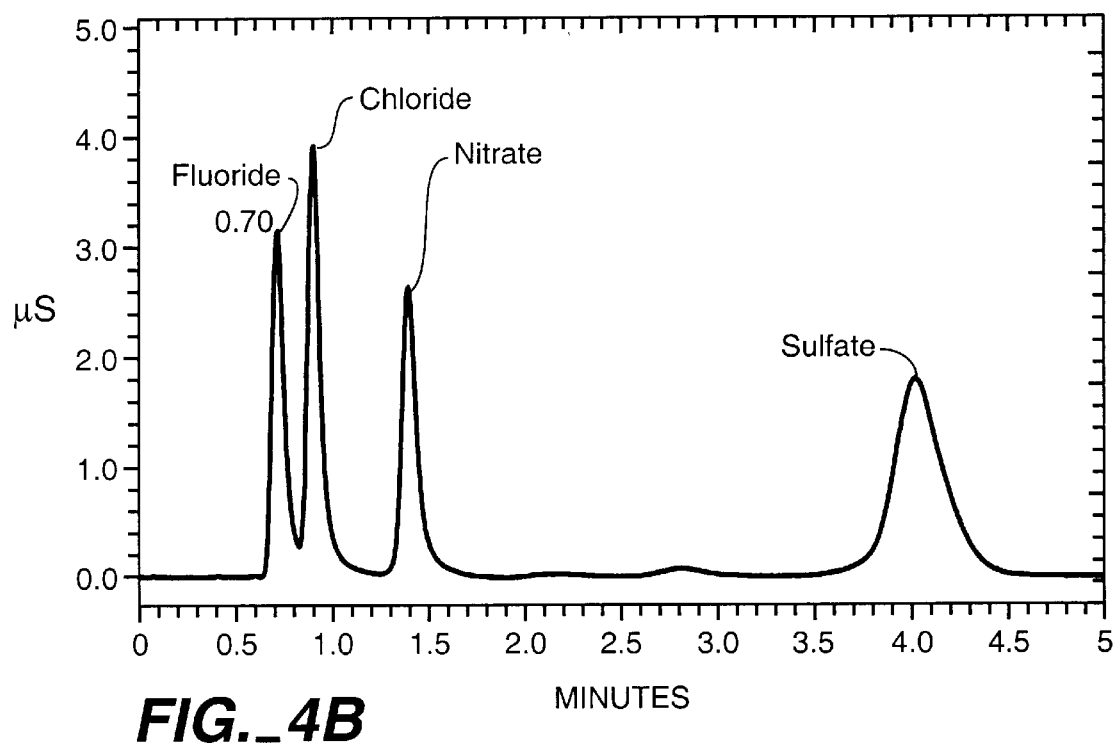
FIG._4B

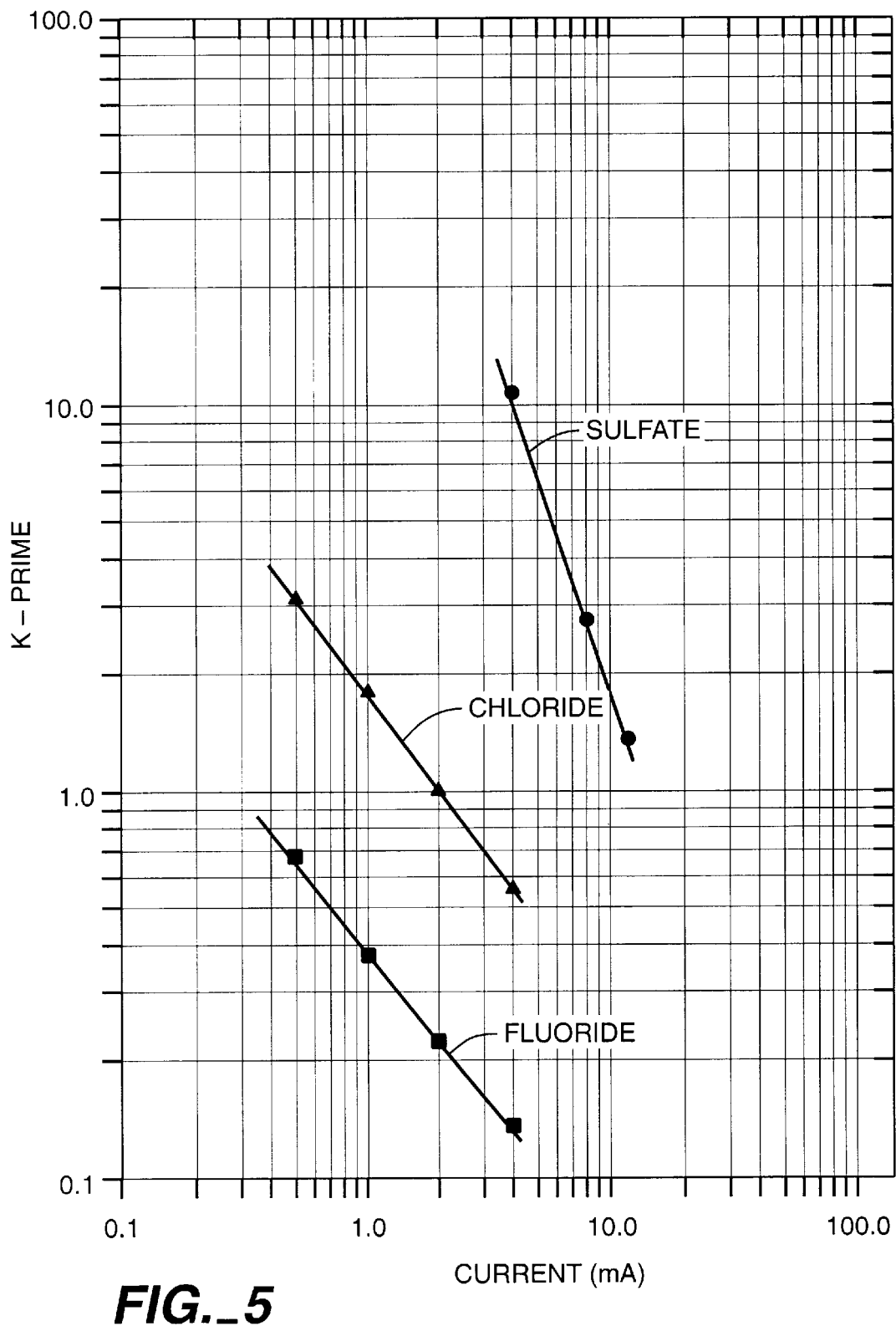
FIG._5

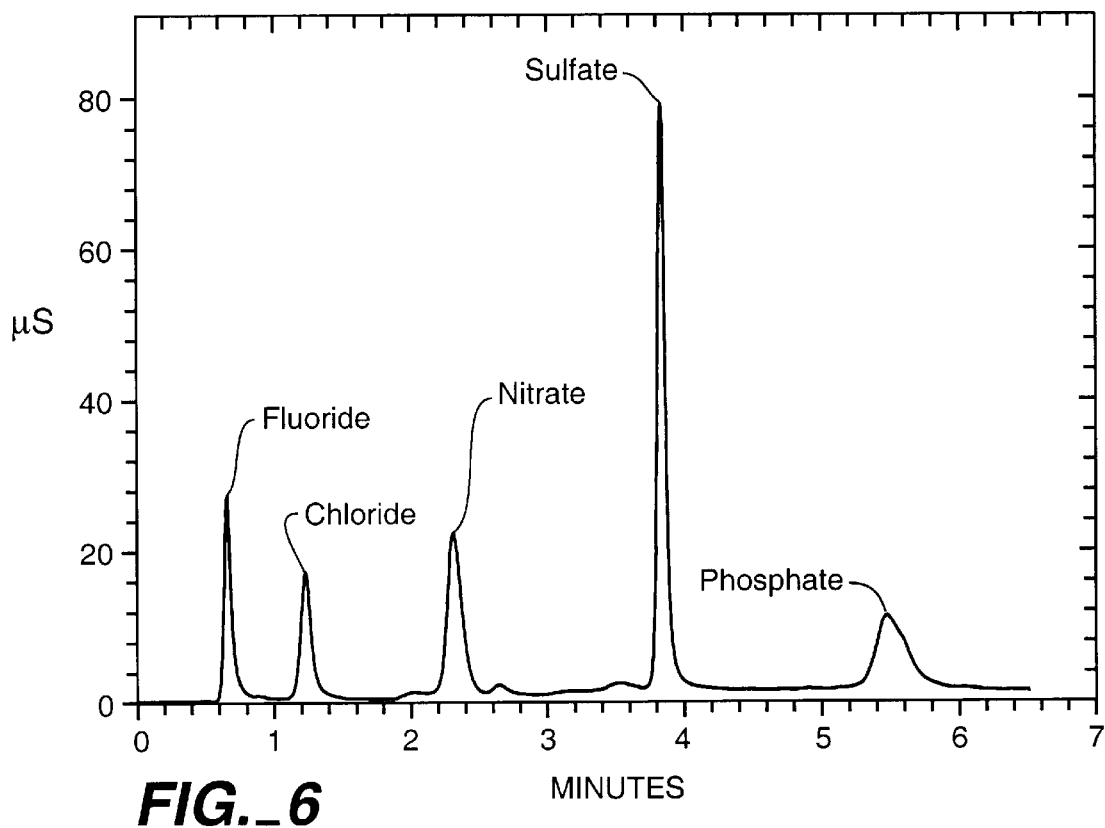
FIG._6
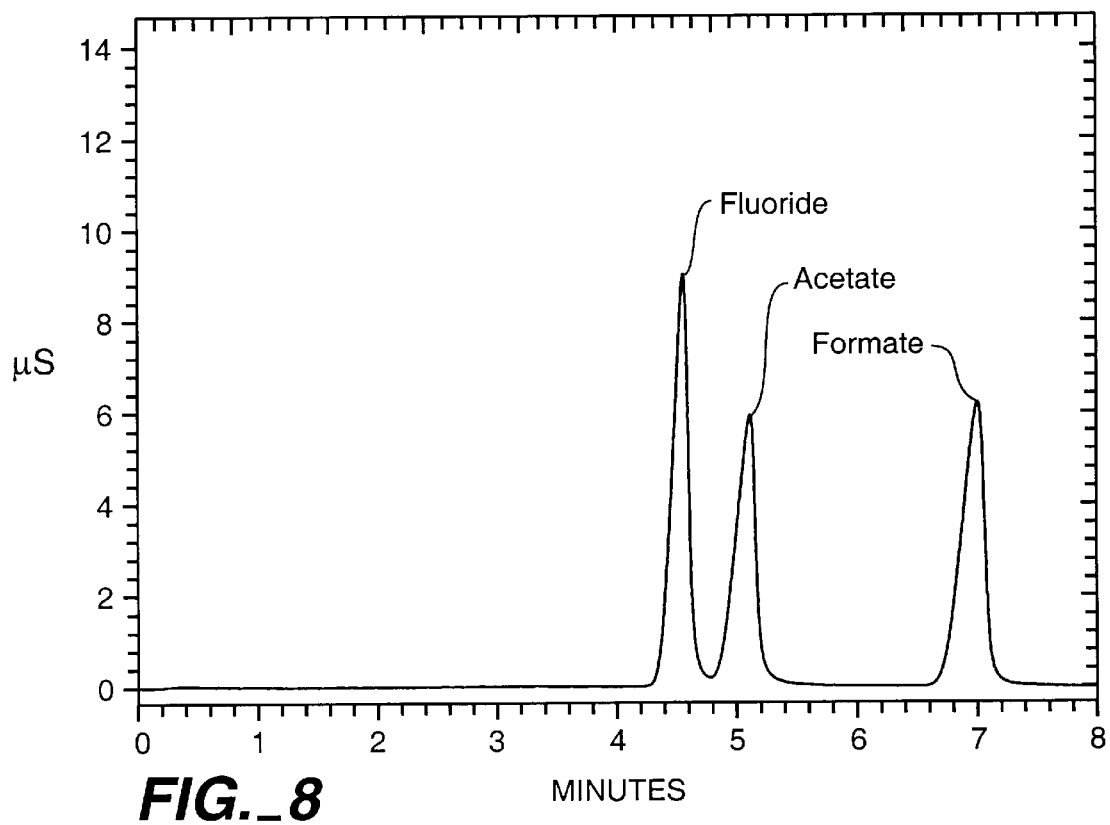
FIG._8

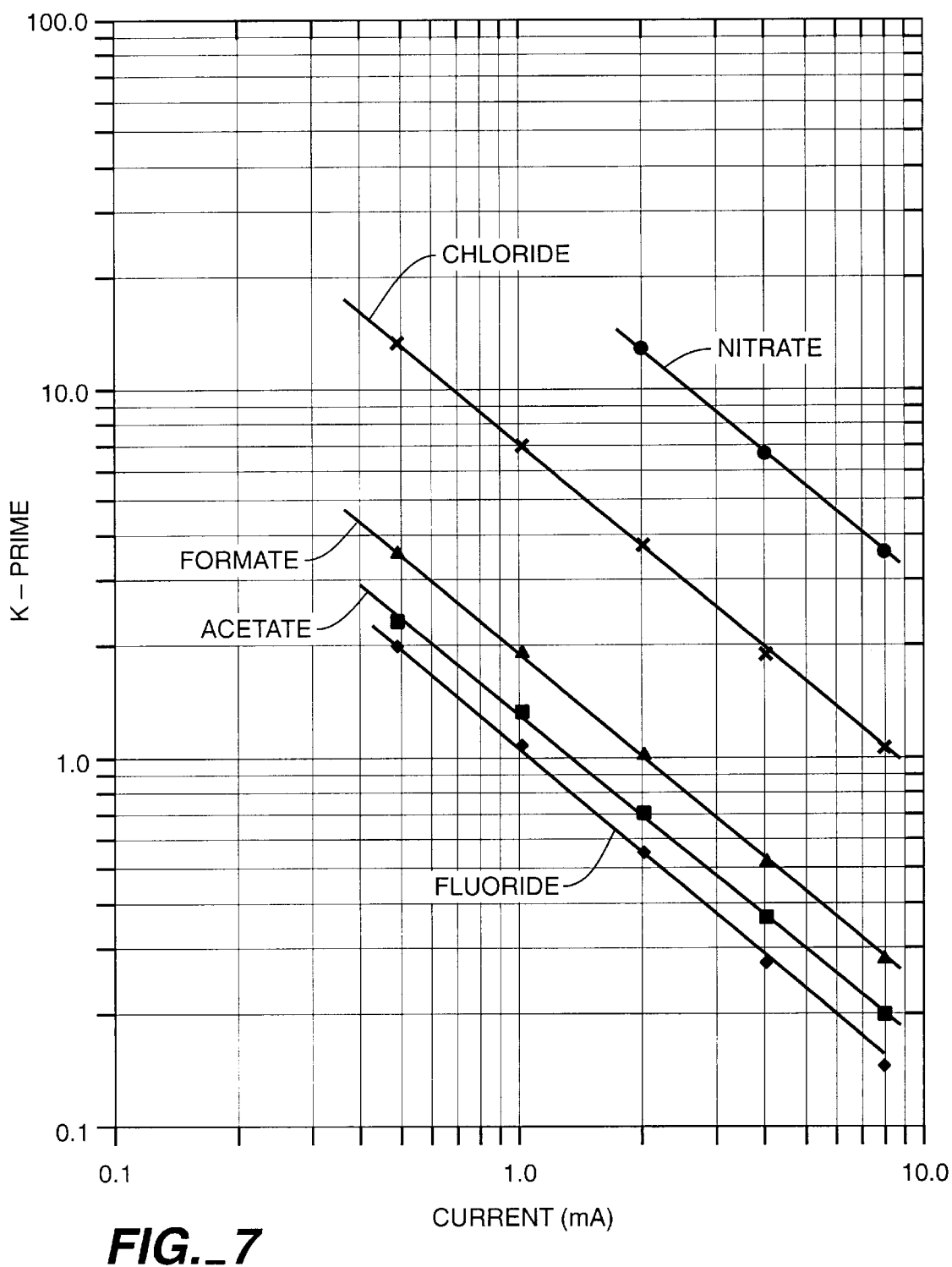
FIG._7

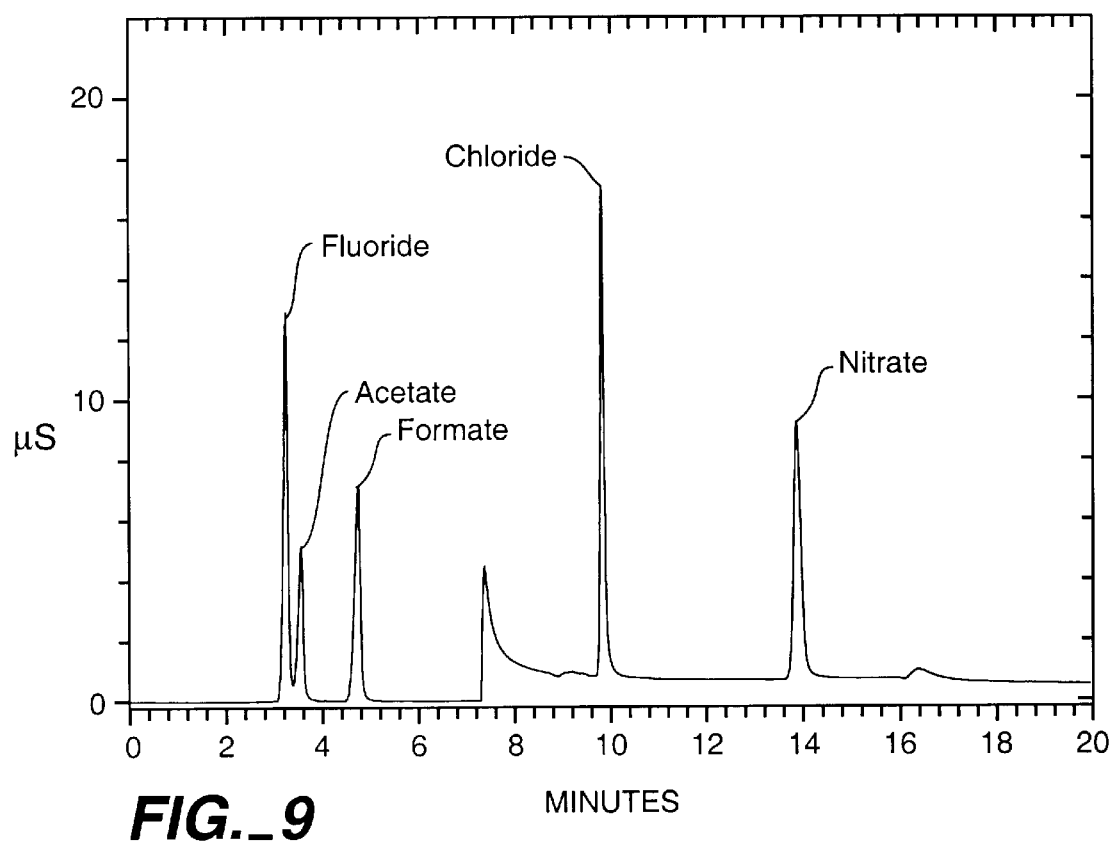
FIG._9
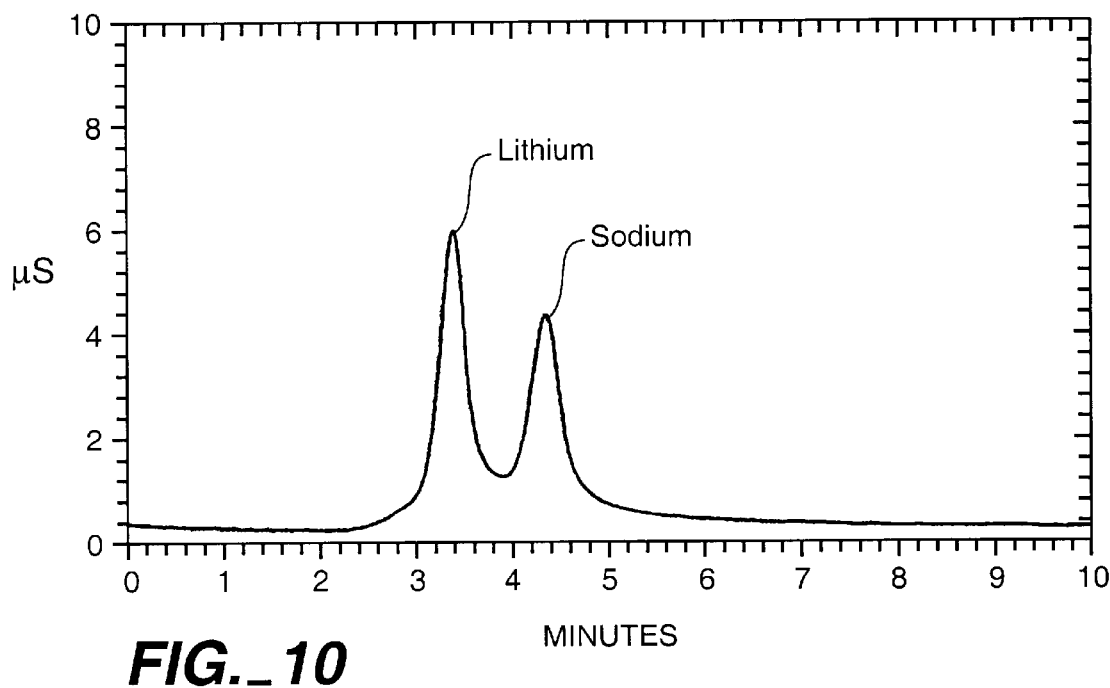
FIG._10

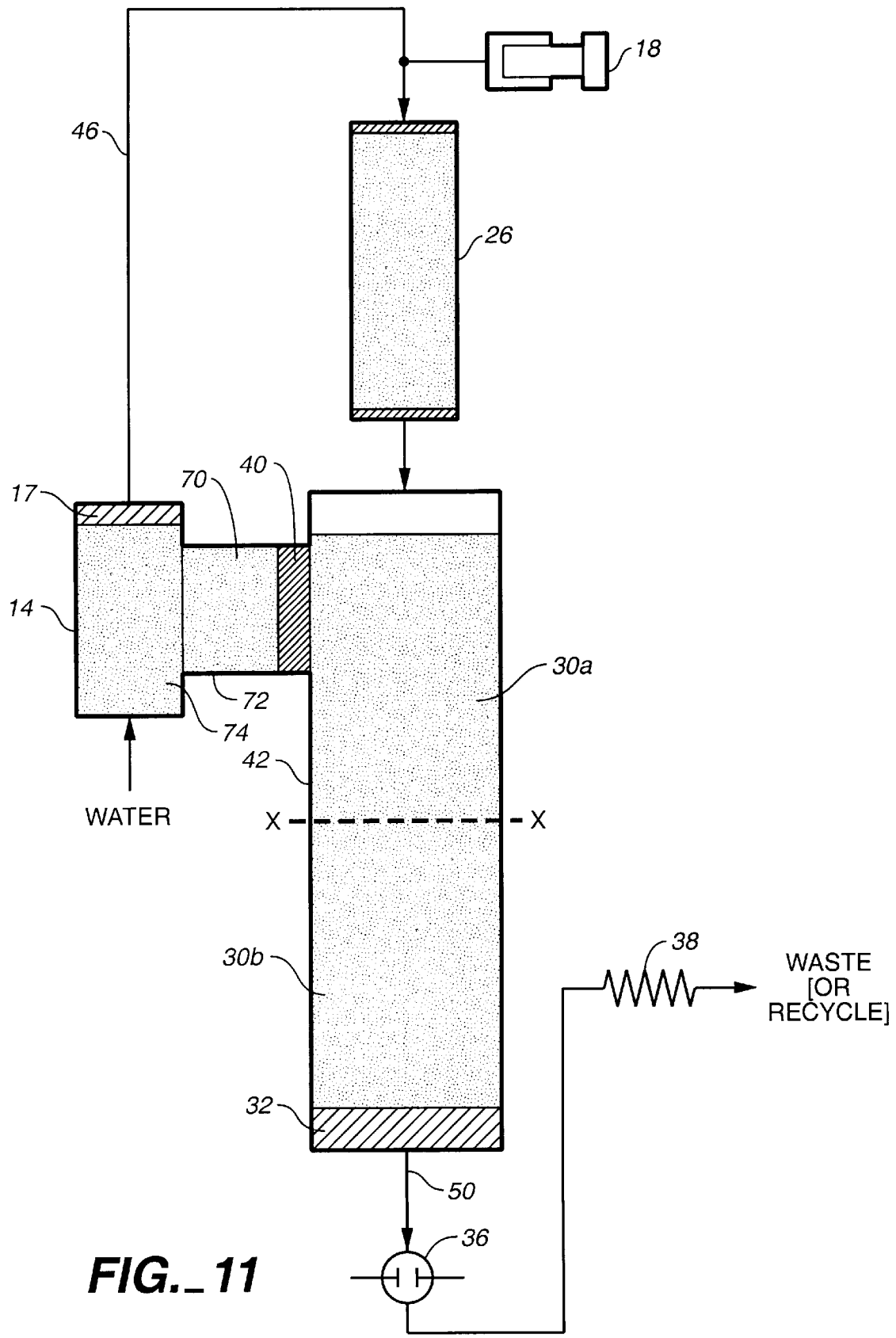
FIG._11

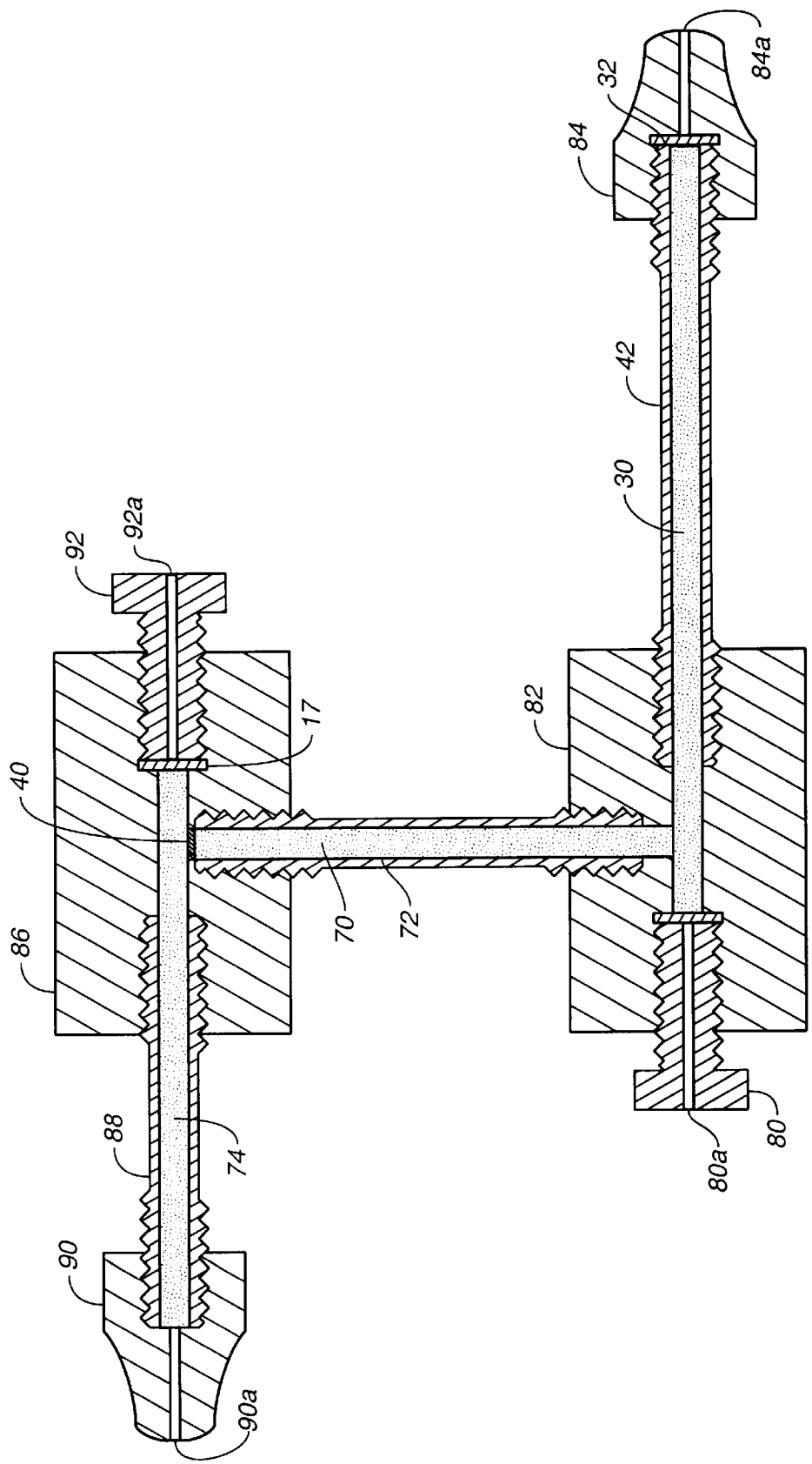
FIG._12

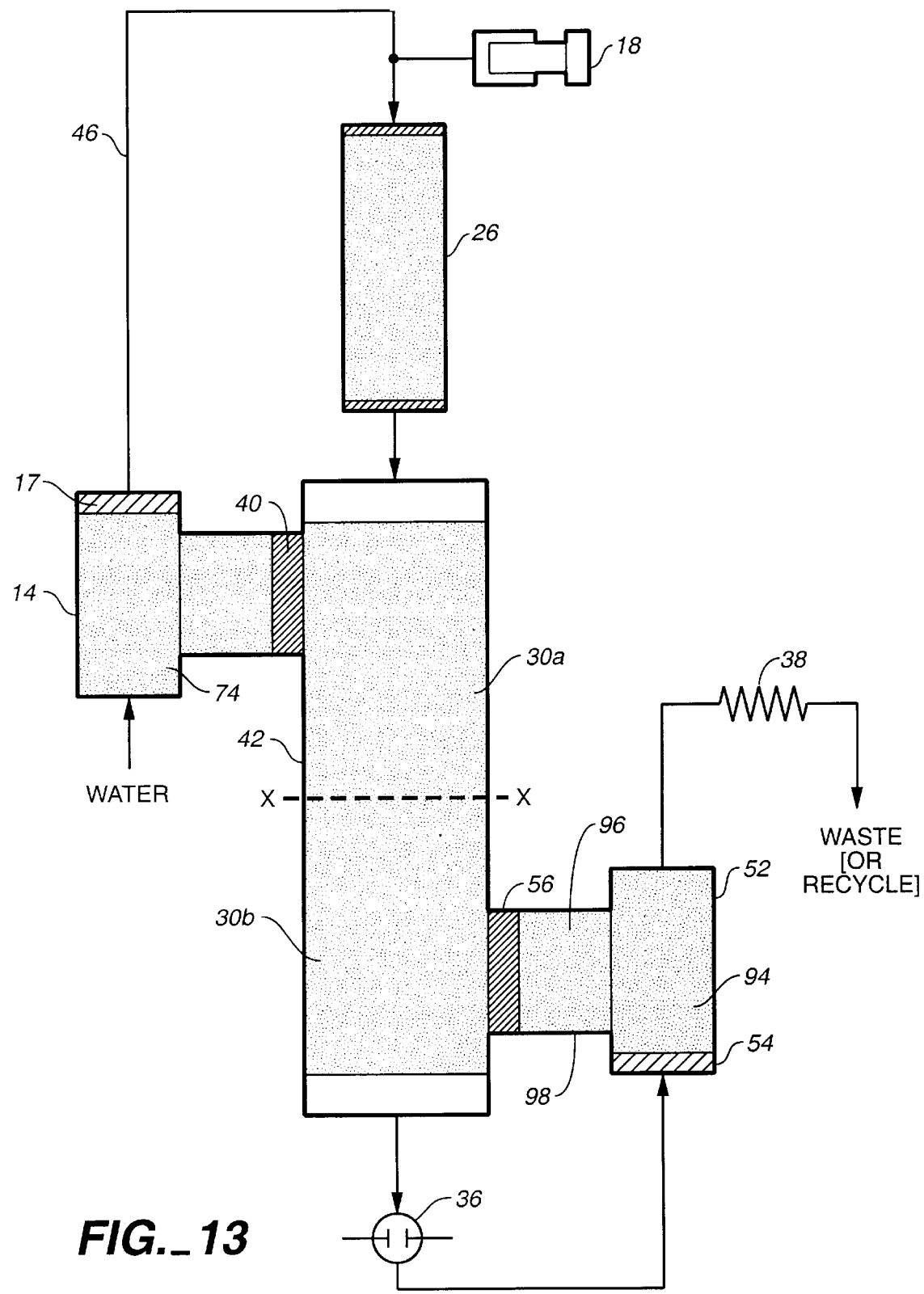
FIG._13

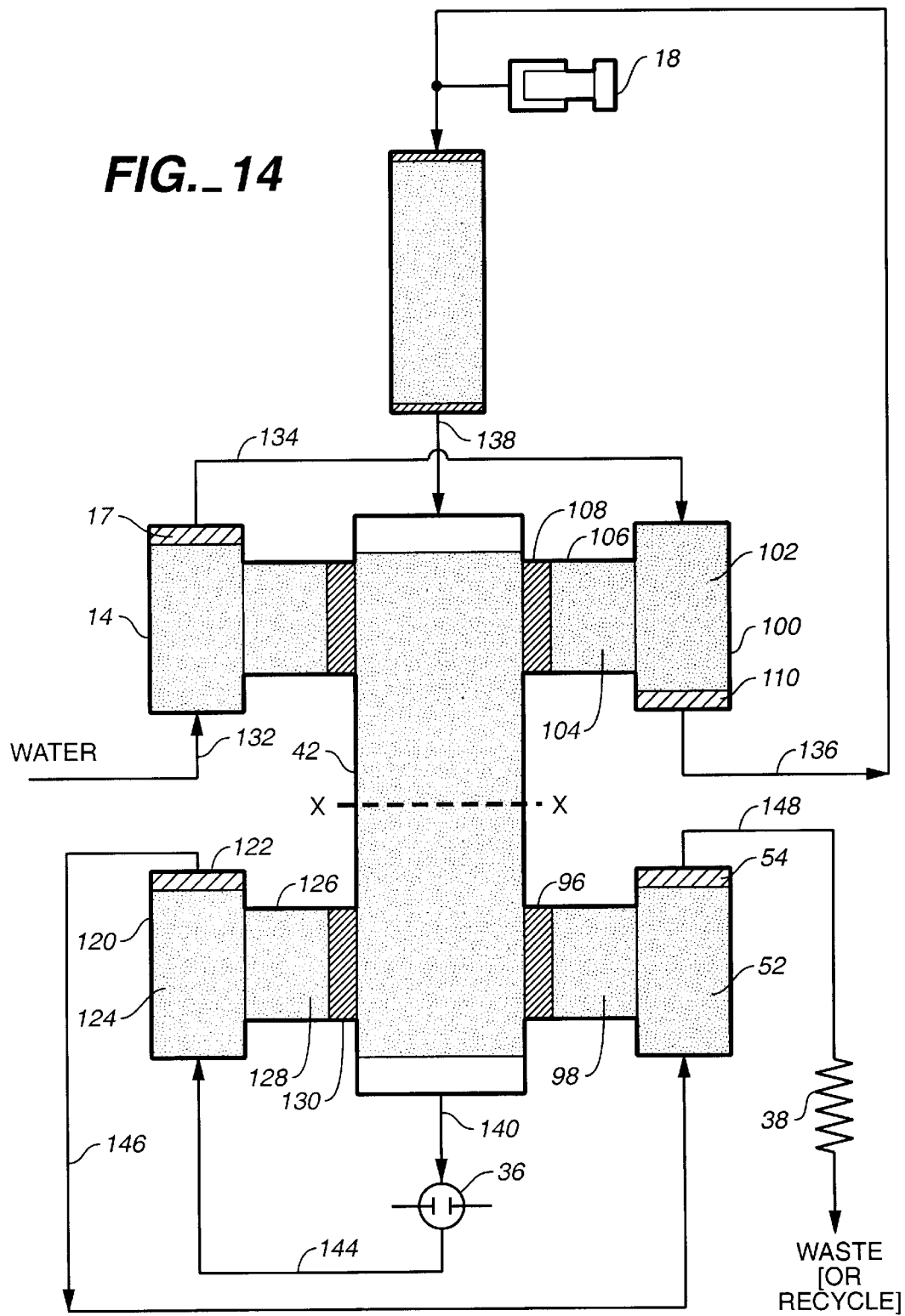
FIG._14

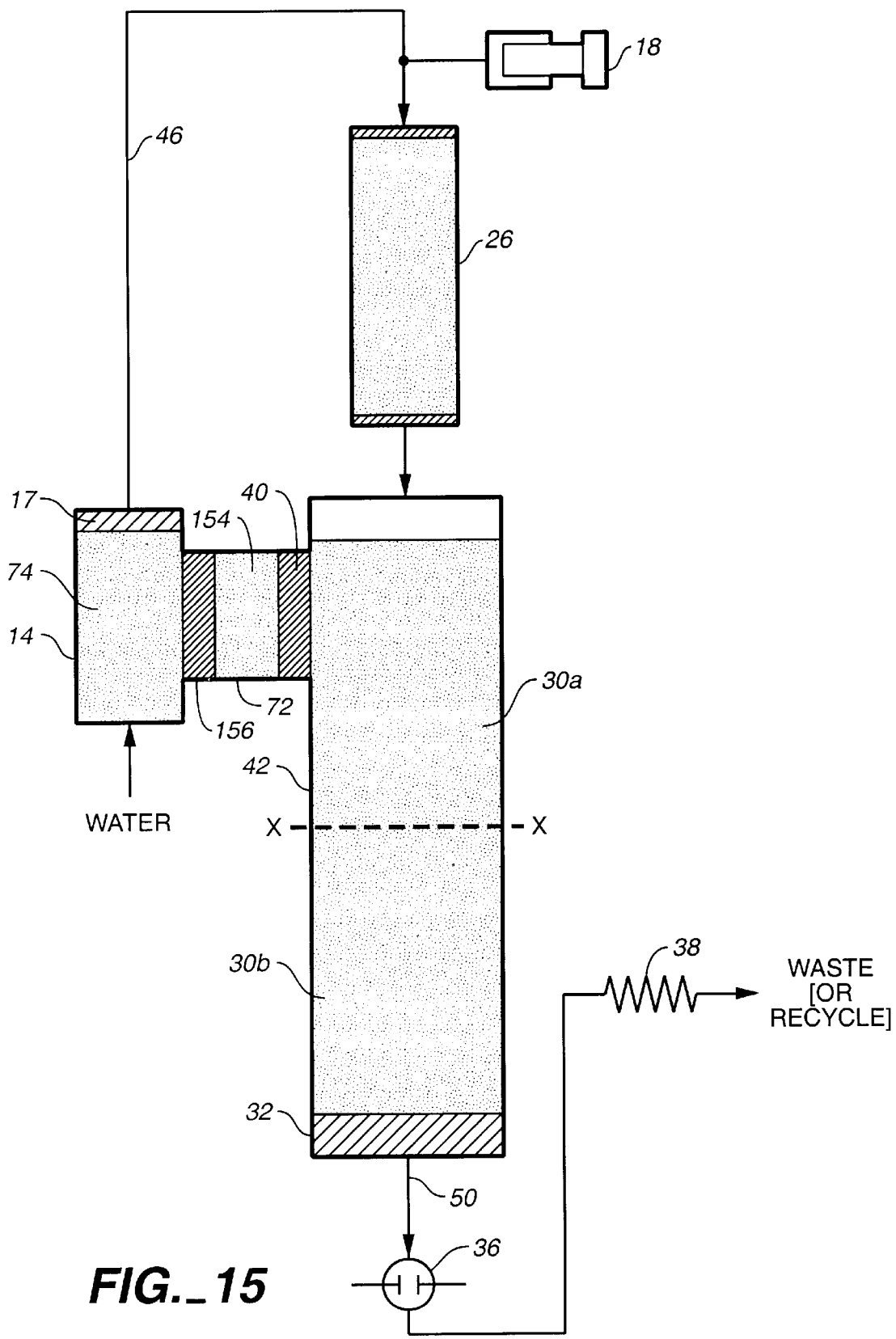
FIG._15

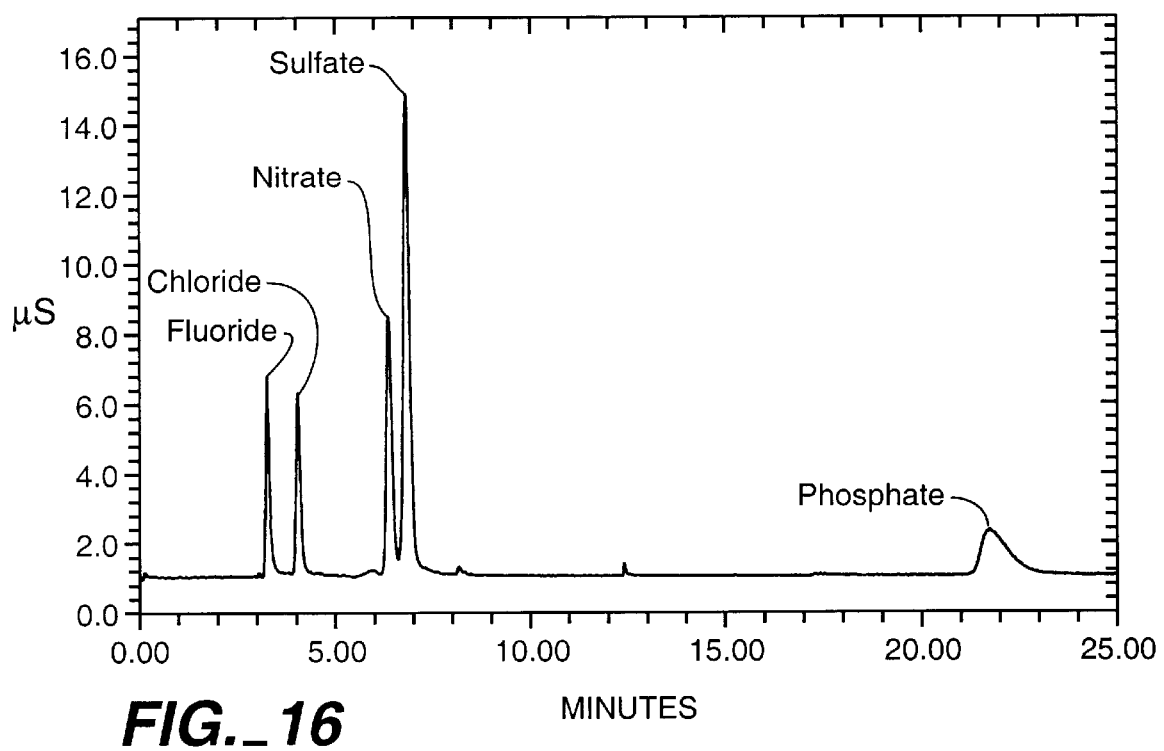
FIG._16
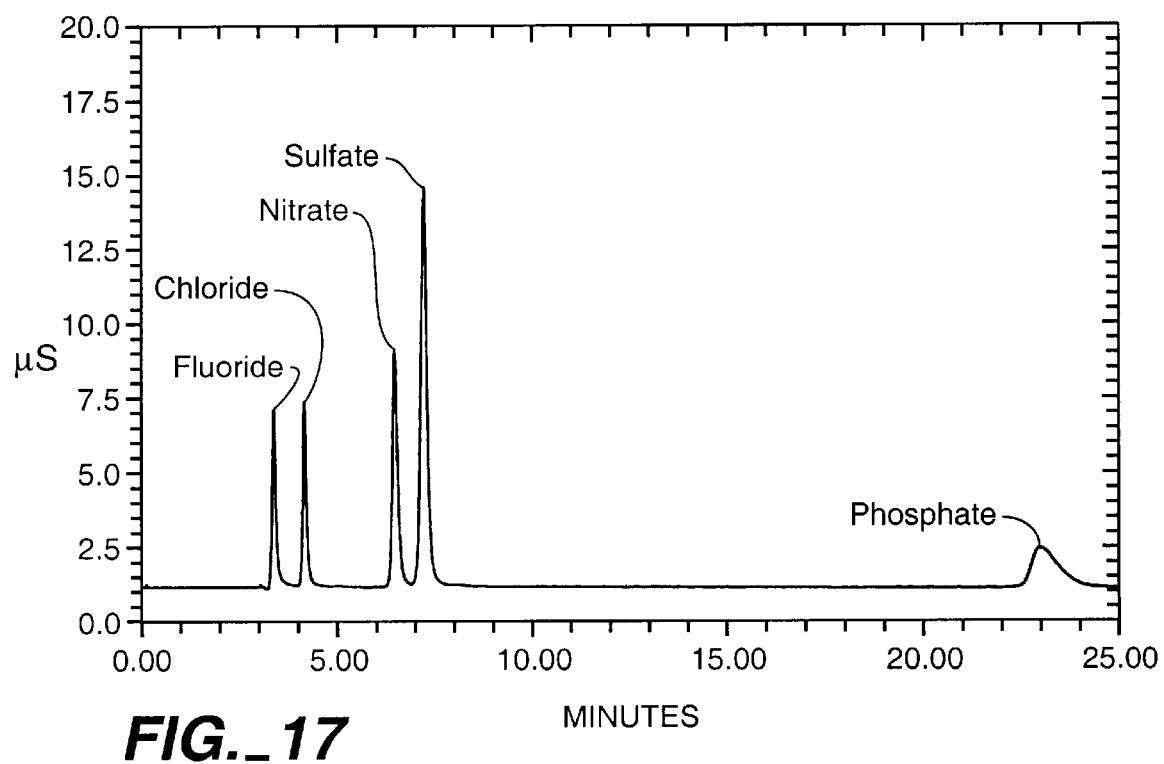
FIG._17

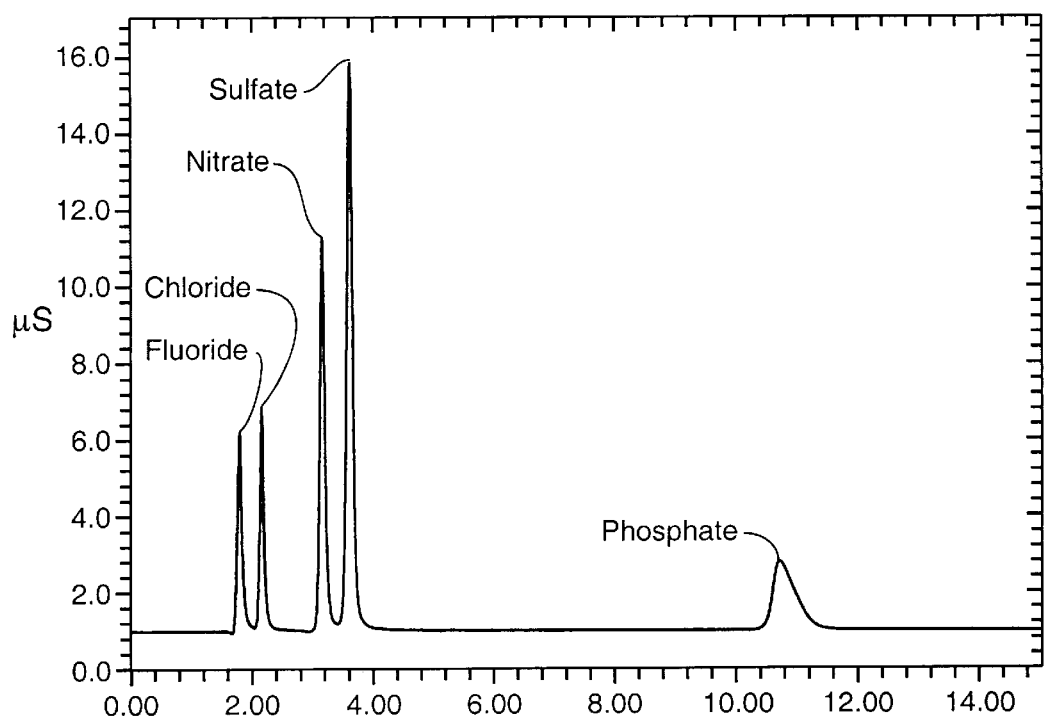
FIG._18
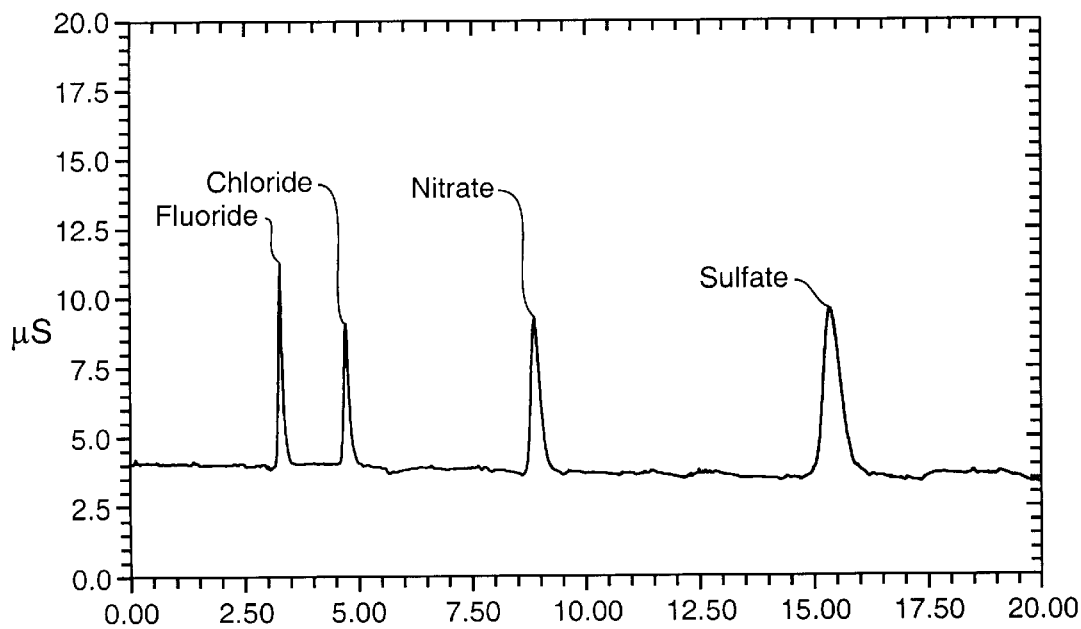
FIG._19

ION CHROMATOGRAPHIC METHOD AND APPARATUS USING A COMBINED SUPPRESSOR AND ELUENT GENERATOR

CROSS-REFERENCE TO RELATED APPLICATION

This application is a continuation-in-part of H. Small U.S. patent application Ser. No. 08/925,813, filed Sep. 4, 1997, now abandoned.

BACKGROUND OF THE INVENTION

The present invention relates to a method and apparatus for ion chromatography using eluents generated within the system.

In liquid chromatography, a sample containing a number of components to be separated is directed through a chromatography separator, typically an ion exchange resin bed. The components are separated on elution from the bed in a solution of eluent. One effective form of liquid chromatography is referred to as ion chromatography. In this known technique, ions to be detected in a sample solution are directed through the separator using an eluent containing an acid or base and thereafter to a suppressor, followed by detection, typically by an electrical conductivity detector. In the suppressor, the electrical conductivity of the electrolyte is suppressed but not that of the separated ions so the latter may be detected by the conductivity detector. This technique is described in detail in U.S. Pat. Nos. 3,897,213, 3,920,397, 3,925,019 and 3,926,559.

There is a general need for a convenient source of high purity acid or base for use as an eluent for liquid chromatography and, particularly, for ion chromatography. In one technique, described in U.S. Pat. No. 5,045,204, an impure acid or base is purified in an eluent generator while flowing through a source channel along a permselective ion exchange membrane which separates the source channel from a product channel. The membrane allows selective passage of cations or anions. An electrical potential is applied between the source channel and the product channel so that the anions or cations of the acid or base pass from the former to the latter to generate therein a base or acid with electrolytically generated hydroxide ions or hydronium ions, respectively. This system requires an aqueous stream of acid or base as a starting source or reservoir.

There is a particular need in ion chromatography for generating an acid or base internally within an ion exchange bed without the requirement of an aqueous acid or base stream source and for simultaneously suppressing conductivity of the eluent in the ion exchange bed after chromatographic separation.

In copending patent application, Ser. No. 08/781,537, filed Jan. 8, 1997, incorporated herein by reference ("the copending application") method and apparatus are disclosed for generating an acid or base eluent in an aqueous stream solely from an ion exchange bed for liquid chromatography and for simultaneously suppressing conductivity of the eluent in the ion exchange bed after chromatographic separation. The copending application describes a system in which a base is generated for the analysis of anions by ion chromatography. The method uses a bed of cation exchange material (e.g., a resin bed) including exchangeable cations. The bed has first and second bed sections arranged in series. The method includes the following steps:

(a) flowing an aqueous feed stream through a first cation exchange bed section while applying an electrical potential to a cathode to generate hydroxide ions in and assist in displacing some of cations on the bed into the aqueous stream to form a cation hydroxide base, (b) flowing a liquid sample stream containing anions to be detected and said eluent through a chromatographic separator portion of said first bed section, further comprising anion exchange material, to separate said anions to be detected, (c) flowing said aqueous separated anion stream through a second bed section substantially free of anion exchange material and including exchangeable hydronium ions, while applying an electrical potential to an anode in the said second bed to generate hydronium ions near said anode, to convert said base to weakly ionized form, and displacing some of said exchangeable hydronium ions with cations from said base, the cations electromigrating from the second bed section to said first bed section along a cation path in the cation exchange/material in the opposite direction to said aqueous feed stream to replenish exchangeable cations displaced from said first bed in step (a), and (d) flowing said suppressor effluent stream past a detector in which the separated anions in said suppressor effluent are detected.

The copending application describes apparatus for anion analysis including the following components:

(a) a sample injection port (b) a flow-through bed of cation exchange material including exchangeable cations, the bed having first and second bed sections arranged in series, the first bed section being in fluid communication with said sample injection port, said first bed section further comprising a chromatographic separator portion including anion exchange material capable of separating anions in an aqueous sample stream flowing through said chromatographic separator portion, the second bed portion being substantially free of anion exchange material and being capable of converting base following in an aqueous stream therethrough into weakly ionized form, (c) first and second electrodes in electrical communication with said first and second bed sections, respectively, the cation exchange material in said first and second bed sections forming a cation path through said cation exchange material between said first and second electrodes, and (d) a power supply for applying a potential between said first and second electrodes.

Since hydrogen and oxygen gases are generated in the ion exchange bed which could interfere with detection, the copending application describes pressurizing the chromatographic effluent prior to detection, such as by use of a flow restrictor. The copending application also describes cation analysis by appropriate reversals of the cation and anion functional components.

SUMMARY OF THE INVENTION

In the present invention, method and apparatus are provided for generating an acid or base eluent in an aqueous solution and for simultaneously suppressing conductivity of the eluent in an ion exchange bed after chromatographic separation in an ion chromatography system.

Referring first to the apparatus, the suppressor and eluent generator comprises: a flow-through suppressor bed of ion exchange resin having exchangeable ions of one charge, positive or negative, having an inlet and an outlet section in fluid communication with fluid inlet and outlet conduits, respectively; an electrode chamber disposed adjacent to said suppressor bed inlet section and having fluid inlet and outlet ports; a flowing aqueous liquid source in fluid communication with said electrode chamber inlet port; a first electrode disposed in said electrode chamber; a barrier separating said suppressor bed from said electrode chamber, said barrier preventing significant liquid flow but permitting transport of ions only of the same charge as said suppressor bed resin exchangeable ions; and a second electrode in electrical communication with said suppressor bed outlet section.

In one embodiment of the ion chromatography apparatus, the generator is used with a flow-through separator bed of ion exchange resin having exchangeable ions of opposite charge to the exchangeable ions of said suppressor bed, said separator bed having a sample inlet port and an effluent outlet port, said electrode chamber outlet port being in fluid communication with said separator bed inlet port, said separator bed outlet being in fluid communication with said suppressor bed inlet port, and a detector downstream from the generator. The aqueous liquid source can be an independent reservoir or can be a recycle conduit from the detector.

Electrical contact between the electrode in an electrode chamber and the barrier may take many forms including direct contact, contact through a charged resin bed bridge, and by the use of an intermediate salt solution.

For anion analysis, one method includes (a) flowing an aqueous liquid sample stream containing anions to be detected and cation hydroxide through a separator bed of anion exchange resin with exchangeable anions to form liquid effluent including separated anions and said cation hydroxide; (b) flowing said aqueous effluent from said separator bed through a flow-through suppressor bed comprising cation exchange resin including exchangeable hydronium ions, so that said cation hydroxide is converted to weakly ionized form, and some of said exchangeable hydronium ions are displaced by cations from said cation hydroxide, said suppressor bed having inlet and outlet sections and inlet and outlet ports, liquid effluent from said suppressor bed flowing through said outlet port; (c) flowing an aqueous liquid through a cathode chamber proximate to said suppressor bed inlet section and separated by a barrier therefrom, said barrier substantially preventing liquid flow between said cathode chamber and said suppressor bed inlet section while providing a cation transport bridge therebetween; (d) applying an electrical potential between a cathode in said cathode chamber and an anode in electrical communication with said suppressor bed outlet section, whereby water is electrolyzed at said anode to generate hydronium ions to cause cations on said cation exchange resin to electromigrate toward said barrier and to be transported across said barrier toward said cathode in said cathode chamber while water in said chamber is electrolyzed to generate hydroxide ions which combine with said transported cations to form cation hydroxide in said cathode chamber; (e) flowing said cation hydroxide from said cathode chamber to the inlet of said separator column; and (f) flowing the effluent liquid from said suppressor bed past a detector in which said separated anions are detected.

After passing the detector in step (f), the effluent liquid can be recycled to said cathode chamber. The system can be used for cation analysis by appropriate reversal of the cation and anion functional components.

In a second embodiment of the suppressor bed, the second electrode is not in direct contact with the suppressor bed. Instead, it is adjacent the suppressor bed outlet section in a second electrode chamber similar to the one described above. In this embodiment, aqueous liquid exiting the detector may be recycled to the inlet of the second electrode chamber. Additional electrode chambers may also be used.

In a third embodiment, similar to the second one, aqueous liquid from a reservoir is pumped to the inlet of the second electrode chamber. Liquid from the outlet of the second electrode chamber is directed to the inlet of the first electrode chamber. Liquid flowing out of the first electrode chamber is directed to the inlet of the separator bed.

An embodiment of a method of anion analysis using the two electrode chambers separated from the suppressor bed includes the following steps: (a) flowing an aqueous liquid sample stream containing anions to be detected and a cation hydroxide through a separator bed of anion exchange resin with exchangeable anions to form a liquid effluent including separated anions and said cation hydroxide; (b) flowing said aqueous liquid effluent from said separator bed through a flow-through suppressor bed comprising cation exchange resin including exchangeable hydronium ions, so that said cation hydroxide is converted to weakly ionized form, and some of said exchangeable hydronium ions are displaced by cations from said cation hydroxide, said suppressor bed having inlet and outlet sections and inlet and outlet ports, liquid effluent from said suppressor bed flowing through said outlet port; (c) flowing an aqueous liquid through an anode chamber proximate to said suppressor bed outlet section and separated by a first barrier therefrom, said first barrier substantially preventing liquid flow between said anode chamber and said suppressor bed outlet section while providing a cation transport bridge therebetween, said aqueous liquid exiting said anode chamber as an anode chamber aqueous liquid effluent; (d) flowing an aqueous liquid through a cathode chamber proximate to said suppressor bed inlet section and separated by a second barrier therefrom, said second barrier substantially preventing liquid flow between said cathode chamber and said suppressor bed inlet section while providing a cation transport bridge therebetween; (e) applying an electrical potential between an anode in said anode chamber and a cathode in said cathode chamber, whereby water is electrolyzed at said anode to generate hydronium ions which are transported across said first barrier to cause cations on said cation exchange resin to electromigrate toward said second barrier and to be transported across said second barrier toward said cathode in said cathode chamber while water in said cathode chamber is electrolyzed to generate hydroxide ions which combine with said transported cations to form cation hydroxide in said cathode chamber; (f) flowing said cation hydroxide from said cathode chamber to the inlet of said separator bed; and (g) flowing the effluent from said suppressor bed past a detector in which said separated anions are detected.

The anode chamber aqueous liquid effluent may be recycled through said cathode chamber. Alternatively, after detection in step (g), the suppressor bed effluent may be recycled through said anode chamber.

In another embodiment, bridging ion exchange resin of the same charge as the charged barrier is disposed in a connector chamber providing an intermediate ion path between said charged barrier and one or more chambers. Also, ion exchange resin may be disposed in the electrode chamber in contact with the first electrode.

In a further embodiment, a second charged barrier of the same charge as the first charged barrier separates said suppressor bed from said electrode chamber. A salt solution is disposed between the first and second charged barriers.

BRIEF DESCRIPTION OF THE DRAWINGS

FIGS. 1–3, 11 and 13–15 illustrate embodiments of suppressor and eluent generators of the present invention in an ion chromatography system.

FIGS. 4–10 and 16–19 are graphical representations of experimental results using the suppressor and eluent generator system of the present invention.

FIG. 12 is a cross-sectional view of the suppressor and eluent generator of FIG. 11.

DETAILED DESCRIPTION OF THE PREFERRED EMBODIMENTS

The present invention is useful for the determination of a large number of ionic species so long as the species to be determined are solely anions or solely cations. A suitable sample includes surface waters, and other liquids such as industrial chemical waste, body fluids, beverages such as fruits and wines and drinking water. When the term ion or ionic species or anion or cation is used herein, they include species in ionic form and components of molecules which are ionizable under the conditions of the present invention.

The method and apparatus of the present invention will first be described with respect to anion analysis and using an anion exchange resin packed bed form of separator. Referring specifically to FIG. 1, chromatography apparatus is schematically illustrated for one embodiment of the present invention. The system includes an independent aqueous stream, such as deionized water 10, suitably from a reservoir, which is pumped to the inlet 12 of electrode chamber 14, including an electrode 17, exiting through electrode chamber outlet 16. For anion analysis, the electrode is a cathode. The effluent from outlet 16 flows past a sample injection port 18 and to the inlet 20 of a flow-through separator bed 22 and out separator bed outlet 24. Typically, the separator bed is contained in a chromatographic column 26 which is packed with a chromatographic separation medium. For the analysis of anions, the separation medium is in the form of an anion exchange resin conventionally used for ion chromatography.

The effluent from separator bed outlet 24 flows to the inlet 28 of suppressor bed 30. As will be described hereinafter, bed 30 is suitably in the form of a cation exchange resin bed used for suppression in anion analysis. A preferred form of resin is a bed packed with resin particles. However, other forms of resin beds can be used, such as disclosed in the copending application, incorporated by reference. Bed 30 serves to suppress the conductivity of the electrolyte in the eluent supplied to separator bed 22 from electrode chamber 14 but not the conductivity of the separated anions. The conductivity of the separated anions is usually enhanced in the suppression process.

In the illustrated embodiment, a suitable sample is supplied through sample injection valve 18 which is carried in a solution of eluent supplied from electrode chamber 14. Anode 32 is disposed at the outlet end of bed 30 in intimate contact with the resin therein. The effluent from bed 30 exits through port 34 and is directed to a detector, preferably in the form of a flow-through conductivity cell 36, for detecting the resolved anions in the effluent.

In conductivity cell 36, the presence of anions produces an electrical signal proportional to the amount of ionic material. Such signal is typically directed from the cell 36 to a conductivity meter, not shown, thus permitting the detection of separated ionic species (anions for anion analysis).

In a preferred embodiment, detection is by ion conductivity and so the present system is described using ion conductivity detector. However, other forms of detectors may be used including absorbance, mass spectrometry, and inductive coupled plasma spectrometry. Detection of the present invention will be described with respect to conductivity detector 36.

The system also includes means for pressurizing the effluent from bed 30 prior to detection to minimize adverse effect of gases (hydrogen and oxygen) generated in the system as will be described hereinafter. As illustrated in FIG. 1, such pressurizing means comprises a flow restrictor 38 downstream of conductivity cell 36 to maintain the ion chromatography system under pressure.

Suppressor bed 30 is suitably formed of cation exchange resin 39 contained within a suitable hollow non-conductive column 42, typically formed of plastic conventionally used for an ion exchange column. It has a cylindrical cavity of a suitable length, e.g., 60 mm long and 4 mm in diameter. It is packed with a high capacity cation exchange resin, e.g., of the sulfonated polystyrene type. The resin is suitably contained in the column by a porous frit which serves to provide an outlet to the column. In the illustrated embodiment, the porous frit is porous electrode (anode) 32 which serves the dual function of containment of the resin and as an electrode. A suitable DC power source, not shown, connects anode 32 and cathode 17 in electrode chamber 14.

Other forms of ion exchange beds can be used in column 42, such as a porous continuous structure with sufficient porosity to permit flow of an aqueous stream at a sufficient rate for use in chromatography without undue pressure drop and with sufficient ion exchange capacity to form a conducting bridge of cations or anions between the electrodes. One form of structure is a porous matrix or a sponge-like material formed of sulfonated, cross-linked polystyrene with a porosity of about 10 to 15% permitting a flow rate of about 0.1 to 3 ml/min. without excessive pressure drop.

A barrier 40 separates bed 30 from the interior of the electrode chamber 14 preventing any significant liquid flow but permitting transport of ions only of the same charge as the charge of exchangeable ions on the resin in bed 30. For anion analysis, barrier 40 is suitably in the form of a cation exchange membrane or plug separating the electrode chamber from the cation exchange resin.

Electrode 17 in electrode chamber 14 also suitably is in the form of an inert metal (e.g., platinum) porous electrode in intimate contact with barrier 40. An electrode is fabricated in a way to permit good irrigation of the electrode/membrane interface when water is passed through electrode chamber 14. The electrode is suitably prepared by crumpling and forming a length of fine platinum wire so as to produce a roughly disc-shaped object that allows easy liquid flow throughout its structure and at the electrode membrane interface. Good contact between the disc-electrode and barrier 40 is maintained simply by arranging that the one press against the other. One means of accomplishing this is to allow either conduit 44 or 46 to penetrate into the electrode chamber and force the electrode against the membrane. The electrode can extend across all or part of the aqueous liquid flow path through electrode chamber 14 to provide intimate contact with the flowing aqueous stream.

Suitable conduits are provided for fluid flow in the system. A conduit 44 is provided to direct the aqueous liquid stream to the inlet 12 of electrode chamber 14. Conduit 46 interconnects electrode chamber outlet 16 and separator bed inlet 20. Conduit 48 interconnects the outlet 24 of separator bed 22 and the inlet 28 of suppressor bed 30. Conduit 50 interconnects the outlet 34 of bed 30 and conductivity cell 36. All of these conduits may be made from narrow bore plastic tubing. However, if desired, conduit 44, 46 and 50 may be made out of stainless steel tubing. When these metal conduits are allowed to touch the platinum electrodes, they make electrical contact with the electrodes as well as being conduits for fluid flow. This provides a means of making electrical contact with the electrodes that is at the same time easy to seal against liquid leakage.

The line X—X is illustrated across the resin 39 in bed 30. For reasons which will be explained below, the resin 39 above the dotted line is predominantly or completely in the form of the cation counter ion of the base used as the electrolyte during separation. Below the line X—X, the resin is predominantly or completely in the hydronium form. The line X—X represents the interface. As used herein, the terms "anion or cation or ion exchange beds" refer to flow-through beds of anion or cation exchange material through which the aqueous liquid stream flows. Unless otherwise stated, the term "cation" excludes hydronium ions and the term "anion" excludes hydroxide ions. Because of its ready availability and known characteristics, a preferred form of ion exchange bed is a packed ion exchange bed of resin particles. It is desirable that the resin particles be tightly packed in the bed, to form a continuous ion bridge or pathway for the flow of ions between electrodes 17 and 32. Also, there must be sufficient spacing for the aqueous stream to flow through the bed without undue pressure drops.

As defined herein, the portion of bed 30 above the line X—X is referred to as the suppressor bed and eluent generator bed inlet section 30a. Conversely, the portion of the bed before the line X—X is referred to as the suppressor bed outlet section 30b. As illustrated, barrier 40 of electrode chamber 14 is disposed adjacent bed inlet section 30a and, therefore, primarily is in the cation form.

One way of forming the bed with the X—X interface is to load the bed with resin having exchangeable ions in cation (e.g., potassium) form and to pump acid (e.g., nitric acid) through the bed to convert the bed outlet section 30b to hydronium form. The amount of hydronium form resin in section 30b may be on the order of about 0.5 meg. and the amount of cation form resin is about 1.3 meg. Alternatively, the resin could be loaded in the hydronium form and a predetermined amount of cation hydroxide pumped through the bed to convert it partially to cation form.

The principle of operation of the system for anion analysis is as follows. An aqueous liquid stream containing anions to be detected and a cation (e.g., potassium) hydroxide flows through separator bed 22 of anion exchange resin with exchangeable anions to form a liquid effluent including separated anions and the cation hydroxide. Anion exchange resin in bed 22 is of a suitable conventional low capacity form used for ion chromatography as illustrated in U.S. Pat. Nos. 3,897,213, 3,920,397, 3,925,019 and 3,926,559. For example, bed 22 typically has a total capacity of about 0.01 to 0.1 milliequivalents. As is conventional, the anion exchange capacity of the separator is low in comparison to that of the suppressor.

The ratio of the capacities of the ion exchange resin in suppressor bed 30 to separator bed 22 may be the same as used for ion chromatography using a conventional packed bed suppressor, e.g. from 10:1 to 1000:1.

For anion analysis, when the water is pumped from reservoir 10, and a polarizing DC potential is applied between cathode 17 and anode 32, the following reactions take place.

The water is electrolyzed and hydronium ions are generated at anode 32 according to the following reaction:

$$H_2O - 2e \rightarrow 2H^+ + \tfrac{1}{2}O_2 \uparrow. \tag{1}$$

This causes cations on the cation exchange resin 39 in bed 30 to migrate to barrier 40. This, in turn, displaces hydronium ions upwardly through bed 30 which causes a similar displacement of cations ahead of them. The cations electromigrate toward the barrier 40 to be transported across the barrier toward cathode 17 in cathode chamber 14 while water is electrolyzed at cathode 17 to generate hydroxide ions according to the following reaction:

$$2H_2O + 2e \rightarrow 2OH^- + H_2 \uparrow. \tag{2}$$

The cations which have transported across the barrier combine with the generated hydroxide ions to form cation hydroxide in cathode chamber 14. Water from reservoir 10 flowing through chamber 14 carries the thus formed cation hydroxide to the sample injection valve where the sample is injected into the separator bed 22. There, the cation hydroxide performs its function as eluent for the injected analyte ions. The effluent from separator bed 22 exits through outlet port 24 and conduit 48 and percolates through the cation form resin in inlet bed section 30a until it reaches the hydronium form resin in bed section 30b where it is neutralized while the cation is retained on the resin. At this point, the anion salts are converted to their respective acids and the cation hydroxide is converted to weakly ionized form.

The suppressed effluent liquid containing the separated anions leaves bed 30 through port 34 and conduit 50 and passes to conductivity cell 36 in which the conductivity of the separated anions is detected.

In an alternative form of the invention, not shown in FIG. 1, the independent source of water could be eliminated and the effluent from conductivity cell 36 recycled in a recycle conduit to electrode chamber inlet port 12 as a source of aqueous liquid 10. In this instance, a stripper device such as a column including anion and cation exchange resin can be disposed in the path of the recycle conduit to strip ions which could interfere with the analysis. Such stripper devices are well known in the art.

The aqueous stream in source 10 may be high purity deionized water. However, for some forms of chromatography, it may be desirable to modify the source with an additive which reacts with the base (acid) generated in electrode chamber 14 to produce eluents of varying potency. For the production of base, such well known additives include a source of carbonic acid, phenol, cyanophenol, and the like. For the production of acid, such additives include m-phenylene diamine, pyridine, lysine and amino propionic acid.

The net result of the electrode reactions and the electromigration of the resin counterions are: the production of cation (e.g., potassium) hydroxide in the region of the cathode, and electrolytic gases at the two electrodes. Specifically, the electrode reactions produce, hydrogen and oxygen which are carried forward into the chromatography system. If these gases are produced in significant volume relative to the liquid flow, their presence can be detrimental to chromatographic efficiency. This potential problem can be eliminated by application of Boyle's law. Specifically, the system can be operated at an elevated pressure (e.g. 100 to 1500 psi) so that the gases are compressed to a volume that is insignificant compared to the flow of the aqueous liquid stream. The pressure necessary to accomplish this depends on the volume of gasses produced. However, for a typical system, a pressure of at least 250 to 500 psi is sufficient. One mode of elevating the pressure is to connect a flow restrictor such as a fine bore coiled tubing 38 downstream of the detector (e.g. three meters of 0.005 in I.D.). This elevates the pressure throughout the chromatography system upstream of the detector. In the present system, it is preferable to construct the conductivity cell to be capable of withstanding a pressure of 1500 psi or more above ambient pressure. A lower pressure of 250 to 500 psi could be used under most conditions. Such system pressure may be high enough to interfere with effective use of membrane suppressors.

When the hydronium ion/cation boundary line X—X is reached, the cation (shown as potassium) hydroxide is neutralized as a conventional suppression according to the following equation:

$$KOH + H^+R^- \rightarrow K^+R^- + H_2O, \quad (3)$$

wherein R is the cation exchange resin. The $K^+R^-$ indicates that the ion exchange resin retains the cation as its exchangeable ion.

The flux of hydronium "upwards" in the resin phase toward bed inlet section 30a is equivalent to the flux of cation hydroxide "downwards" in the mobile phase toward bed outlet section 30b. Since the balance prevails at different current levels, the position of the hydronium/cation boundary line X—X remains fixed. Thus, the system operates as a continuous generator and suppressor of cation hydroxide. In this regard, this end result is similar to the copending application. However, in contrast to the copending application, in the present system the cation hydroxide flows for a time outside bed 30 before returning to it. This exterior pathway permits the use a conventional separator resin bed 22. It is preferable to control the concentration of acid (or base) produced in electrode chamber 14. To do so, the current which is directly related to concentration should be controlled. A feed-back loop may be provided to assure sufficient voltage to deliver the predetermined current. Thus, the current is monitored and when the resistance changes, the potential is correspondingly changed by the feed-back loop. Therefore, the voltage is a slave to the reading of the current. Thus, it is preferable to supply a variable output potential system of this type (e.g., sold under the designation Electrophoresis Power Supply EPS 600 by Pharmacia Biotech and Model 220 Programmable Current Source by Keithley).

During operation of the system for anion analysis, there is a limit on the ability to generate suppressed eluent indefinitely. For example, the analyte ions (e.g., chloride and bromide) can be injected in their sodium salts. The anions are deposited on the anion separator where they are resolved and finally elute from the column as separated peaks of potassium chloride and potassium bromide. The sodium ions, on the other hand, pass through the separator and are deposited by ion exchange onto the cation exchange resin in bed 30. Therefore, a small amount of sodium is added to the cation exchange bed 30. Thus, the amount of hydronium form resin in bed 30 is diminished by an amount equal to the amount of sodium deposited. For a small single sample, this amount is very small relative to the total amount of hydronium ions. However, with a great many samples, it is possible that all of the hydronium form resin could be displaced by the cations. A simple way to avoid this potential problem over a long-term use is to convert the analytes to acid form prior to injection. Then, no additional middle cations are added to the cation "pool" in bed 30. Since the cation is trapped in a perpetually circling pool, the hydronium form resin should be fixed at line X—X and the conditions for indefinite generation and suppression are preserved.

The system of FIG. 1 has been described with respect to a system for the analysis of anions. However, the system is also applicable to the analysis of cations. In this instance, electrode 32 is a cathode and electrode 17 is an anode. The polarity of the resins is reversed. Thus, the resin in separator bed 22 is a cation exchange resin and the resin in bed 30 is an anion exchange resin. In this instance, instead of generating cation hydroxide in electrode chamber 14, an acid is generated for use as the electrolyte in the eluent in separator bed 22.

Briefly described, the system works as follows for the cation analysis. The aqueous liquid stream containing cations to be detected and an acid electrolyte aqueous eluent are directed through separator bed 22 including cation exchange resin. The effluent from separator bed 22 flows through suppressor bed 30 including anion exchange resin with exchangeable hydroxide ions. The acid in the eluent is converted to weakly ionized form. Some of the exchangeable hydroxide is displaced by anions from the acid.

In cation analysis, the aqueous stream from source 10 flows through electrode chamber 14 containing an anode separated by barrier 40 preventing liquid flow between anode chamber 14 and suppressor bed 30 while providing an anion transport bridge therebetween. An electrical potential is applied between the negatively charged electrode 32 and positively charged electrode 17. Water is electrolyzed at electrode 32 to generate hydroxide to cause anions on the anion exchange resin bed to electromigrate toward barrier 40 to be transported across the barrier toward the positively charged anode 17 in the electrode chamber 14 while water in chamber 14 is electrolyzed to generate hydronium ions which combine with the transported anions to form acid in the electrode chamber 14. The aqueous liquid eluent containing the thus-generated acid from the chamber 14 flows to the separator bed 22. The effluent liquid from the suppressor bed 30 flows past detector 36 in which separated cations are detected.

The exchangeable cations or anions for suppressor bed 30 and, thus for the acid or base electrolyte in the aqueous eluent, must also be sufficiently water soluble in base or acid form to be used at the desired concentrations. Suitable cations are metals, preferably alkali metals such as sodium, potassium, lithium and cesium. Known packing materials for high capacity ion exchange resin beds are suitable for this purpose. Typically, the resin support particles may be in the potassium or sodium form. Potassium is a particularly effective exchangeable cation because of its high conductance. Suitable other cations are tetramethyl ammonium and tetraethyl ammonium. Analogously, suitable exchangeable anions for cation analysis include chloride, sulfate and methane sulfonate. Typically, resin support particles for these exchangeable anions include Dowex 1 and Dowex 2.

Another embodiment of the invention is illustrated in FIG. 2. Since many of the components of the embodiments of FIGS. 1 and 2 are the same, like parts will be designated with like numbers. Similarly, the description of like parts will be incorporated by reference. Like the embodiment in FIG. 1, the FIG. 2 embodiment may be used with a conventional packed ion exchange resin bed separator column.

The principal difference between the embodiments of FIGS. 1 and 2 is that in the latter one, there are two external electrode chambers rather than one so that the analyte ions are prevented from contacting any electrodes. To accommodate this difference, there is a change in the flow scheme through the system.

Referring specifically to FIG. 2, aqueous liquid from source 10 travels through conduit 44 to electrode chamber 14 containing electrode 17 in which the electrolyte is generated in the same manner described with respect to FIG. 1. For anion analysis, the cation hydroxide (e.g., potassium hydroxide) flows through conduit 46 carrying with it sample injected through injection port 18 into separator bed 22 contained by chromatographic column 26. As in the embodiment of FIG. 1, separation is performed in separator bed 22 in a conventional manner.

The effluent from separator bed 22 flows into suppressor bed 30 of the same general type described above. In this instance, electrode 32 disposed in the outlet section of bed 30 is eliminated. Its function is performed by a second electrode chamber 52 including an electrode 54. The interior of electrode chamber 52 is separated from the separator and eluent generator bed 30 by a barrier 56 which is in intimate contact with porous electrode 54. The construction of electrode chamber 52 and its electrode 54 and barrier 56 are the same as described above with respect to electrode chamber 14. The difference between electrode chambers 14 and 52 is that the electrode 17 is of opposite polarity to electrode 54 to provide an electrical path when D.C. current is impressed between the electrodes. In that regard, electrode chamber 52 serves an analogous function to electrode 32. For anion analysis, electrode 54 is an anode while electrode 17 is a cathode. The reaction (1) described above occurs in electrode chamber 52.

Aqueous liquid (e.g. water) is pumped into electrode chamber 54 from a suitable source. One source is to recycle effluent from conductivity cell 36 downstream of flow restrictor 38 through recycle conduit 58. The effluent from electrode chamber 52 flows to waste in conduit 60.

The hydronium ions formed in electrode chamber 52 by the anodic reaction (1) pass through barrier 56 into bed section 30b where they displace hydronium ions and, in turn, cations flow "upward" through the bed 30 in the same manner as described above. The cations pass across barrier 40 into electrode chamber 14 where cathodic reaction (2) occurs and wherein they receive an equivalent number of hydroxide ions generated at the cathode. The cation hydroxide thus formed is carried as the electrolyte eluent in conduit 46 and into separator bed 22 in the same manner as described above. The ion exchange resin is retained in column 42 by plastic frits 62a and 62b.

An advantage of the device of FIG. 2 over that of FIG. 1 is that analyte ions are prevented from contacting either of the electrodes. Since the electrodes are respectively oxidizing and reducing environments, this avoids possible electroactive analyte ions from undergoing reactions at the electrodes which would compromise their subsequent detection and measurement. Such isolation of the electrodes voids this potential problem.

FIG. 3 illustrates a third embodiment of the invention using two electrode chambers like that of FIG. 2. The difference between FIGS. 1 and 2 is in the aqueous liquid flow system. Specifically, in FIG. 3, water from an independent source 64 is directed through conduit 66 into electrode chamber 52 and from there through conduit 68 to electrode chamber 14. Thus, the effluent from electrode chamber 52 flows through conduit 68 to form the aqueous stream flowing through electrode chamber 14 which serves as the eluent flowing through conduit 46 past sample injection valve 18 and into separator bed 22. Otherwise, the operation of these systems are the same. As in the embodiments of FIGS. 1 and 2, the line X—X provides a dividing line between the inlet bed section 30a and the outlet bed section 30b. For anion analysis, the portion above the line X—X is primarily in the cation form and the portion below the line X—X primarily in the hydronium ion form.

As with the embodiment of FIG. 1, by appropriate changes in the polarity of electrodes 17 and 56 and of the resin employed in separator bed 22 and suppressor 30, the system can be converted to one for use for cation analysis.

Another embodiment, illustrated schematically in FIG. 11, is similar to FIG. 1, except that it includes a resin bridge between barrier 40 and electrode 17 in electrode chamber 14. Like numbers will be used to designate like parts in the embodiments of FIGS. 1 and 11. The same flows and reactions take place for these two figures, and so the description of FIG. 1 is incorporated by reference.

In the schematic diagram of FIG. 11, ion exchange resin in the form of a connecting ion exchange resin bed 70 is packed into a column 72 which, in turn, is in open communication with and in direct contact with an ion exchange resin bed 74 in electrode chamber 14. The combination of charged beds 70 and 74 provides electrical communication between charged barrier 40 and electrode 17.

FIG. 12 is a cross-sectional view of the apparatus of FIG. 11. As illustrated, water flows through inlet channel 80a of end cap 80 threadedly received by block 82. Suppressor bed 30 is contained within a cylindrical bore defined by block 82, column 42 and end cap 84 into which the other end of column 42 is threadedly received. The suppressed liquid flows through channel 84a of end cap 82. Electrode 32, an anode for generating a base, is in the form of a porous flow-through platinum electrode transverse to flow and retained in place by a pressure fit between column 42 and end cap 84.

Column 72 serving as a container for bridging or connecting ion exchange resin beds 30 and 74. Columns 42 and 72 form a T-connection within block 82 to provide open communication between resin 30 and resin 70. Column 72 is threadedly reserved into the top of block 82 at one end and into the bottom of block 86 at its other end. A similar T-connector is disposed in block 86. Ion exchange barrier 40 is pressure fit on the lower end of column 88 formed in block 86. Ion exchange resin bed 74 is contained within column 88 which mates with end cap 90 including a flow-through port 90a. Electrode 17 is held in place by end cap 90. Column 88 is threadedly received in a recess in end cap 90 at one end and in a recess in block 86. Column 88 is held in place at its other end by end cap 92 which includes an outlet channel 92a. The function of the device illustrated in FIG. 12 is described with respect to FIGS. 1 and 11.

A suitable resin-bridge ion reflux device of the type illustrated in FIGS. 11 and 12 for KOH generation is constructed as follows. Electrode chamber 14 (4–6 mm ID×20–40 mm length) is packed with a sulfonated resin in K$^+$ form and includes a perforated Pt cathode 17 at its outlet. Column 42 (4–6 mm ID×40–60 mm length) consists of an upstream bed (20–30 mm length) of a sulfonated resin in K$^+$ form and a downstream bed (20–30 mm length) of a sulfonated resin in H$^+$ form and includes a perforated Pt cathode at its outlet. Electrode chamber 14 is in electrical communication with the upstream bed (K$^+$ ion form) in column 42 through an ion exchange resin bridge which consists of a cation exchange membrane plug and a bed of a sulfonated resin in K$^+$ form.

In another embodiment, illustrated in FIG. 13, an ion exchange bed resin bridge between the barrier 40 and electrode 17 in electrode chamber 14 is also used in second electrode chamber 52 to provide electrical contact between barrier 56 and electrode 54 of the type shown in FIG. 2. Like parts in FIGS. 2, 12 and 13 will be designated with like numbers. In contrast to the embodiment of FIGS. 11 and 12, the Pt electrode 54 is in chamber 52 rather than in column 42. For generation of KOH, chamber 52 is a column (e.g., 4–6 mm ID×20–40 mm length) packed with an ion exchange resin bed 94 of high capacity (e.g. sulfonated) resin in $H^+$ form and equipped with perforated Pt electrode 54 at its inlet. Chamber 14 is connected to the upstream bed ($K^+$ ion form) of the suppressor bed 30 using a resin bridge. The $H^+$ ion generated in chamber 52 connected to the downstream bed portion ($H^+$ ion form) of suppressor bed 30 uses a similar resin bridge. Ion exchange resin in the form of a connecting ion exchange resin bed 96 is packed into a column 98 which, in turn, is in open communication with and in direct contact with anion exchange resin bed 94 in electrode chamber 52. The combination of charged beds 94 and 96 provides electrical communication between charged barrier 56 and electrode 54. The resin bridge consists of a cation exchange membrane plug and a bed of a sulfonated resin in $K^+$ or $H^+$ form. Under the electrical field, ion reflux of $K^+$ ions and chemical suppression of $OH^-$ ions occur in the suppressor bed 30, and $H^+$ ions generated at the anode of the $H^+$ ion generation column migrate continuously through the resin bridge into suppressor bed 30 to supply $H^+$ ions used for chemical suppression of $OH^-$ ions.

In another embodiment of the resin-bridge device, two or more electrode chambers are used for KOH generation or for $H^+$ ion generation or for both. This increases the capability of generating KOH at significantly higher concentrations without excessive heating. A resin-bridge suppressor device employing two KOH generation electrode chambers and two $H^+$ ion generation electrode chambers is illustrated in FIG. 14. Like parts of other figures will be designated with like numbers.

Referring FIG. 14, a third electrode chamber 100 contains an ion exchange resin bed 102 which is an open communication with a connecting ion exchange resin bed 104 contained in column 106. Beds 102 and 104 provide electrical communication between barrier 108 and electrode 110 at the outlet of chamber 100. The components of electrode chamber 100 and the electrical communication between electrode 110 and barrier 108 are as described with respect to electrode chamber 14 and the ion exchange resin bed bridge described in FIG. 13.

A fourth electrode chamber 120 is included of the same type as electrode chamber 52 as illustrated in FIG. 13. It includes an electrode 122 at its outlet, an ion exchange resin bed 124 in the electrode chamber, and column 126 connected column 42 and containing an ion exchange resin 128 forming electrical communication between electrode 122 and barrier 130 as described with respect to electrode chamber 52.

Flow through the system is modified as follows. An aqueous stream (water) enters one end of electrode chamber 14 in line 132 and flows through the chamber past electrode 17 in line 134 and into the inlet port of electrode chamber 100. From there, the outlet flows through electrode 110 in line 136 to sample injector 18 as separator column 22 in line 138 of the separator bed.

In a downstream portion of the column, the suppressed liquid flows through line 140 to conductivity cell 36, line 144 to electrode chamber 120 and through a porous electrode 122 in line 146 back to the inlet port of electrode chamber 52. After passing through chamber 52 and porous electrode 54, the outlet fluid flows through line 148 to restrictor 38 and to waste.

In this device, the KOH solution generated at the first electrode chamber is fed into the second electrode chamber generating KOH to boost the total concentration of generated KOH. For example, if each electrode chamber generating KOH is applied with a current of 40 mA to generate 25 mM of KOH at 1.0 mL/min, the resin bridge ion device with two electrode chambers generating KOH is able to produce 50 mM of KOH at 1.0 mL/min. The KOH solution leaving the second column is then used for ion chromatographic separation. The two electrode chambers generating KOH are connected to the same suppressor bed to share a common $K^+$ ion source. Additional electrode chambers generating KOH generation columns can be added to further increase the concentration of generated KOH. A significant advantage of the resin bridge ion reflux device with multiple electrode chambers generating KOH and $H^+$ is that the operating voltage of the device is lower because the applied current is now distributed among the multiple electrode chambers. Therefore, higher currents can be applied to generate KOH at higher concentrations without being limited by excessive heating.

The electrical connection can also be accomplished through the use of a salt-bridge as shown in FIG. 15. As illustrated, the KOH generation column is connected to the upstream bed ($K^+$ ion form) of the suppressor bed using a salt bridge which consists of a short column (e.g., 4–6 mm ID×10–20 mm length) filled with a concentrated solution of a potassium salt and fitted with impermeable cation exchange membrane plugs at both ends. The operation of the salt-bridge ion reflux device is otherwise similar to the resin-bridge ion reflux device.

Referring specifically to FIG. 15, like parts will be designated like numbers with respect to the resin-bridge device of FIG. 11 using a single electrode chamber. In this instance, electrically conducting salt solution 154 is contained within column 72 and forms an electrically conductive bridge between barrier 40 and a similar barrier 156. Any salt solution can be used as long as it provides an electrical connection between anode 32 and cathode 17 across membrane 40, salt bridge 154 and barrier 156 and through ion exchange resin 74.

Barriers at both ends of the salt bridge contain the salt solution in place. Otherwise, it would flow into resin bed 30 or resin bed 74. Thus, containment by such barriers is used in such a two-phase system. The salt solution in connector column 72 is of the type which permits the transport of ions out of the upstream portion of bed 30 and into exchange resin bed 74 of electrode chamber 52 for formation of KOH.

The following equipment was used to perform a series of experiments set forth in the Examples by way of illustrating the present invention.

The apparatus was constructed as illustrated in FIG. 1. This particular apparatus is referred to later as IRD-2. The suppressor and eluent generator column 42 and the electrode chamber 14 were constructed from a single block of plastic. Column 42 was separated from electrode chamber 14 by barrier 40 in the form of a disk of cation ion exchange membrane. The membrane used was supplied by Membrane International of Glenrock, N.J. (designation MAI-7000 cation exchange membrane). Barrier 40 is preferably of sufficient thickness to withstand the pressure of HPLC. Suitably, the membrane is at least about 0.1 mm thick and preferably at least about 0.1 mm thick. Electrode 17 can be in the form of a crumpled length of platinum wire pressed against the membrane.

The cation exchange resin used in bed 30 was either Dowex 50WX8 200–400 mesh or a similar styrenedivinylbenzene-based resin by Dionex Corporation, which was also 8% cross linked and had an average particle diameter of about 18 micrometers.

The resin in bed 30 was initially loaded in the potassium ion form. Then, a precisely measured amount of 0.01M nitric acid was pumped through the bed to convert the lower, outlet section to the hydronium form. In most cases, the amount of hydronium form resin was 0.5 milliequivalent. The remaining upper portion of resin in the potassium form was about 1.3 milliequivalents.

(Alternatively, the resin could be loaded as the hydronium form and a precisely measured amount of potassium hydroxide pumped through the bed to convert it partially to the potassium form. Layering precisely measured amounts of hydronium and potassium form resins in column 42 would be another way of preparing this compartment.)

The chromatographic pump, sample injector, and conductivity cell and detector were typical ion chromatography system components manufactured by the Dionex Corporation of Sunnyvale, Calif.

The flow restrictor was a coil of fine bore coiled tubing (e.g., three meters of 0.005 in I.D.).

Anion separator columns were standard, commercially available products of Dionex Corporation.

One of two DC power supplies were used; Electrophoresis Power Supply EPS 600 by Pharmacia Biotech and Model 220 Programmable Current Source by Keithley.

EXAMPLE 1

Separator column: Dionex AG-11 column, 50 mm long, 4 mm internal diameter.

Sample size: 10 microliters.

Sample: a solution containing fluoride, chloride, nitrate and sulfate; 0.0001M in each ion.

Flow rate of water: 1 ml./min.

Power supply: EPS 600 set to deliver a constant current of 6 milliamps. The output potential (measured) was 30 V.

FIGS. 4A and 4B show the chromatograms obtained for two injections made eight hours apart. During the eight hours, the current was maintained through the bed 30. This experiment illustrates the ability of the system to deliver eluent of reproducible concentration and to suppress it after several hours of continuous use. Subsequent experiments demonstrated that this behavior can be repeated after several days of use.

EXAMPLE 2

With the same apparatus and conditions used in Example 1, the elution times of individual ions were measured at various applied currents. Ions were injected as 0.0001M solutions. The results follow.

| Ion | current (mA) | voltage (V) | $t_E$ (min.) | $t_E - t_V$ (min.) | k' |
|---|---|---|---|---|---|
| sulfate | 3.9 | 22 | 7.47 | 6.84 | 10.86 |
| sulfate | 8.1 | 39 | 2.47 | 1.84 | 2.92 |
| sulfate | 12.0 | 47 | 1.5 | 0.87 | 1.38 |
| chloride | 0.5 | 6 | 2.73 | 2.1 | 3.33 |
| chloride | 1.0 | 9 | 1.82 | 1.19 | 1.89 |
| chloride | 1.9 | 14 | 1.3 | 0.67 | 1.06 |
| chloride | 3.9 | 24 | 1.01 | 0.38 | 0.6 |
| fluoride | 0.5 | 6 | 1.07 | 0.44 | 0.7 |
| fluoride | 1.0 | 9 | 0.87 | 0.24 | 0.38 |

-continued

| Ion | current (mA) | voltage (V) | $t_E$ (min.) | $t_E - t_V$ (min.) | k' |
|---|---|---|---|---|---|
| fluoride | 1.9 | 14 | 0.78 | 0.15 | 0.23 |
| fluoride | 3.9 | 24 | 0.72 | 0.09 | 0.14 |

$t_E$ is the elution time of the ion
$t_V$ is the time required to clear the void volume of the separator bed
k' is defined as $(t_E - t_V)/t_V$ The results are expressed graphically in FIG. 5 which shows how the elution of an ion may be manipulated simply by varying the current passed through the system.

EXAMPLE 3

This experiment used the Keithley 220 power supply to apply current to IRD-2 in a programmed series of steps. Otherwise, the conditions were the same as in Examples 1 and 2.

The currents applied to IRD-2 and the duration of the steps were as follows:

| current(mA): | 2 3 4 5 6 7 8 9 10 11 12 13 14 15 16 17 18 19 20 |
|---|---|
| duration(sec.) | 60 60 1 1 1 1 1 1 60 1 1 1 1 1 1 1 1 1 216 |

A sample containing the anions fluoride, chloride, nitrate, sulfate and phosphate at concentrations, respectively, 2, 3, 10, 15 and 15 mg./liter, was injected while the current in IRD-2 was 2 mA. At the instant of injection, the current program was started.

FIG. 6 shows the chromatogram obtained and illustrates how a stepped current may be used to elute ions of widely differing ion exchange affinities within a practical time interval.

EXAMPLE 4

In this experiment, the separator column used was a Dionex AS-11 column, 250 mm long, 4 mm internal diameter.

The power supply was the Keithley Model 220.

The elution times of the ions fluoride, acetate, formate, chloride and nitrate were established for various currents applied to IRD-2. The results follow and are expressed graphically in FIG. 7.

| Ion | current (mA) | $t_E$ (min.) | $t_E - t_V$ (min.) | k' |
|---|---|---|---|---|
| fluoride | 0.5 | 4.47 | 2.97 | 1.98 |
| fluoride | 1.0 | 3.16 | 1.66 | 1.11 |
| fluoride | 2.0 | 2.34 | 0.84 | 0.56 |
| fluoride | 4.0 | 1.92 | 0.42 | 0.28 |
| fluoride | 8.0 | 1.72 | 0.22 | 0.147 |
| acetate | 0.5 | 5.03 | 3.53 | 2.35 |
| acetate | 1.0 | 3.49 | 1.99 | 1.33 |
| acetate | 2.0 | 2.57 | 1.07 | 0.71 |
| acetate | 4.0 | 2.05 | 0.55 | 0.37 |
| acetate | 8.0 | 1.80 | 0.30 | 0.20 |
| formate | 0.5 | 6.93 | 5.43 | 3.62 |
| formate | 1.0 | 4.53 | 3.03 | 2.02 |
| formate | 2.0 | 3.11 | 1.61 | 1.07 |
| formate | 4.0 | 2.31 | 0.81 | 0.54 |
| formate | 8.0 | 1.92 | 0.42 | 0.28 |

-continued

| Ion | current (mA) | $t_E$ (min.) | $t_E - t_V$ (min.) | k' |
|---|---|---|---|---|
| chloride | 0.5 | 20.75 | 19.25 | 12.8 |
| chloride | 1.0 | 12.05 | 10.55 | 7.03 |
| chloride | 2.0 | 7.13 | 5.63 | 3.75 |
| chloride | 4.0 | 4.4 | 2.9 | 1.93 |
| chloride | 8.0 | 3.1 | 1.6 | 1.07 |
| nitrate | 2.0 | 20.3 | 18.8 | 12.5 |
| nitrate | 4.0 | 11.7 | 10.2 | 6.8 |
| nitrate | 8.0 | 6.97 | 5.47 | 3.65 |

EXAMPLE 5

Using the Dionex AS-11 column and a current of 0.5 mA applied to the IRD-2, a mixture of fluoride, acetate and formate ions was separated. The concentration of the injected ions was 0.0001M in each case. The chromatograph is shown in FIG. 8. The peaks for fluoride, acetate and formate were at, respectively, 4.57, 5.12 and 7.00 min.

EXAMPLE 6

Using the Dionex AS-11 column, the five anions, fluoride, acetate, formate, chloride and nitrate were separated while the current programmed to bed 30 was cycled between 0.5 mA for 10 min. and 8.0 mA for 15 min.

The sample mixture (0.0001M in each ion) was injected 2.5 min. after the transition from 8 mA to 0.5 mA. The chromatogram is shown in FIG. 9. The peaks for fluoride, acetate, formate, chloride and nitrate were at, respectively, 3.23, 3.53, 4.72, 9.80 and 13.85 min.

This is another example of how programmed current can accomplish the separation of ions of widely differing ion exchange affinities.

EXAMPLE 7

In this example, a flow-through sponge-like cation exchange bed is formed to act as the eluent generator/suppressor.

Styrene and divinyl benzene are copolymerized in the presence of an appropriate catalyst and a porogen. A porogen is an added material which, when removed after the polymerization is complete, creates a macroporosity in the polymerized structure. This porosity should be such that it provides for a ready flow of liquids through the polymer phase while at the same time providing adequate areas of contact between the polymer and liquid phase. The porogen can be a finely divided solid which can be easily removed by dissolution in acid or base (e.g., calcium carbonate or silica), or it can be a solvent which is rejected by the polymer as it forms and is subsequently displaced by another solvent or water. Suitable liquid porogens include an alcohol, e.g., used in the manner described in *Analytical Chemistry*, Vol. 68, No.2, pp. 315–321, Jan. 15, 1996.

After the porogen is removed, the polymer is sulfonated by commonly known sulfonating agents such as concentrated sulfuric acid or chlorosulfonic acid.

A suitable shape for the polymer is a cylindrical rod which, after sulfonation and conversion to a suitable metal ion form can be placed in the cylindrical cavity of the eluent/generator column. Preferably, the ion exchange rod is introduced into the column in a slightly shrunken form so that in its typical use environment it swells to form a tight fit with the wall of the column and the cation exchange membranes that separate the ion exchange rod from the electrode compartments.

As a final step, the rod is treated so that the part closest to the outlet is in the hydronium form while the part closest to the inlet is in a metal cation form such as the potassium form. This is accomplished by treating the rod with the appropriate amount of acid, or by electrochemically displacing potassium ions with hydronium ions.

EXAMPLE 8

A system similar to that illustrated by FIG. 3 was used for cation analysis. In this case, the ion exchange resin bed 30 was an 8% cross-linked polystyrene/divinylbenzene based anion exchange resin. The upper portion 30*a* was in the methane sulfonate form, the lower portion 30*b* was in the hydroxide form. The ion exchange resin bed was 4 mm in diameter and 100 mm in length. The portion, 30*b*, in the hydroxide form was approximately 25 mm in length. This portion was prepared by electrochemically displacing methane sulfonate ions with hydroxide ions.

The membranes separating the anion exchange resin from the anode and cathode compartments compartment were anion exchange membranes: Ultrex membrane AMI-7001 supplied by Membrane International, N.J.

This distance between the electrodes was approximately 50 mm.

The separator bed used in conjunction with the eluent/generator was a Dionex cation separator designated CG12A 4X50 mm.

A power supply was connected so that electrode of compartment 14 was the anode and electrode of compartment 52 was the cathode. The power supply maintained a constant current of 2.0 mA. Water was pumped at 1 ml./min. These conditions generated methane sulfonic acid in electrode compartment 14, approximately 0.001 2M in concentration.

A sample containing lithium ion at 1.0 mg/L and sodium at 5 mg./L was injected and the output of the conductivity cell gave the chromatogram shown in FIG. 10, showing the baseline resolution of lithium (first peak) and sodium.

EXAMPLE 9

A resin-bridge device, as illustrated in FIG. 12, was constructed as follows. The KOH generation column (4-mm ID×45-mm length) was packed with a 18-$\mu$m sulfonated resin in $K^+$ form having a perforated Pt cathode at its outlet. Suppressor column 42 (4-mm ID×80-mm length) consisted of an upstream bed (45-mm length) of a 18-$\mu$m sulfonated resin in $K^+$ form and a downstream bed (35-mm length) of a 18-$\mu$m sulfonated resin in $H^+$ form. Column 42 was equipped with a perforated Pt cathode at its outlet. The KOH generation column was connected to the upstream bed ($K^+$ ion form) of the suppressor bed using a resin bridge column (4-mm ID×35-mm length) which consisted of a cation exchange membrane plug (0.054 inch in thickness) and a bed of a 18-$\mu$m sulfonated resin in $K^+$ form.

The device was tested under an applied current of 12.5 mA and a flow rate of 0.5 mL/min. The applied voltage was 80 V. The concentration of KOH generated was 15.5 mM. FIG. 16 shows the separation of five common anions on a Dionex AS-11 column using the ion reflux device. The chromatogram obtained with the device is similar to that obtained with the conventional ion chromatographic system.

EXAMPLE 10

A resin-bridge device, as illustrated in FIG. 13, was constructed. The KOH generating electrode chamber 14

(4-mm ID×35-mm long column) was packed with a 18-μm sulfonated resin in K⁺ form and equipped with a perforated Pt cathode at its outlet. Column 42 (4-mm ID×95-mm length) consisted of an upstream bed (35-mm length) of a 18-μm sulfonated resin in K⁺ form and a downstream bed (60-mm length) of a 18-μm sulfonated resin in H⁺ form. The H⁺ generating electrode chamber 54 (e.g., 4-mm ID×35 mm length) was packed with a 18μm sulfonated resin in H⁺ form and equipped with a perforated Pt anode at its outlet.

The device was tested under an applied current of 12.5 mA and a flow rate of 0.5 mL/min. The applied voltage was 85 V. FIG. 17 shows the separation of five anions on a Dionex AS-11 column obtained using the device. The results demonstrate that the resin-bridge device is a viable approach to implement the ion reflux concept.

EXAMPLE 11

A resin-bridge device designed to employ two KOH generating electrode chambers and two H⁺ ion generating electrode chambers, as illustrated in FIG. 14, was constructed and tested. This device has two cathodes and two anodes. The effects of different electrode configurations on the device operating voltage were investigated; Cathodes A and B were electrodes in the two KOH generation columns and Anodes C and D were electrodes in the two H⁺ ion generation columns. The tests confirmed that the use of multiple KOH generating electrodes and H⁺ ion generating electrode reduces the operating voltage of the device and allows the device to operate under higher applied currents (to generate KOH at higher concentrations) without excessive heating.

The device was also tested for separation of anions using a 4-mm AS-11 column. FIG. 18 shows the representative chromatogram obtained when the IRD was operated under an applied current of 25 mA to generate and suppress 15.5 mM KOH at 1.0 mL/min.

EXAMPLE 12

A salt-bridge apparatus, as illustrated in FIG. 15, was constructed and tested. The KOH generating electrode chamber (4-mm ID×45-mm length) was packed with a 18-μm sulfonated resin in K⁺ form and equipped with a perforated Pt cathode at its outlet. The column 42 (4-mm ID×80-mm length) included of an upstream bed (45-mm length) of a 18-μm sulfonated resin in K⁺ form and a downstream bed (35-mm length) of a 18-μm sulfonated resin in H⁺ form. Column 42 was equipped with a perforated Pt cathode at its outlet. The KOH generation column was connected to the upstream bed (K⁺ ion form) of column 42 using salt-bridge (⅛-inch ID×40-mm length) which was filled with a saturated solution of potassium oxalate and fitted with cation exchange membrane plugs as barriers at both ends.

The device was tested under an applied current of 10 mA and a flow rate of 0.5 mL/min. The applied voltage was 110 V. FIG. 19 shows the separation of fluoride, chloride, nitrate, and sulfate on an AS-11 column obtained using the salt-bridge apparatus.

What is claimed is:

1. A suppressor and eluent generator for ion chromatography comprising:
    (a) a flow-through suppressor bed of ion exchange resin having exchangeable ions of one charge, positive or negative, having an inlet and an outlet section in fluid communication with fluid inlet and outlet conduits, respectively,
    (b) an eluent generator electrode chamber disposed adjacent to said suppressor bed inlet section and having fluid inlet and outlet ports,
    (c) a flowing aqueous liquid source in fluid communication with said electrode chamber inlet port,
    (d) a first electrode disposed in said electrode chamber,
    (e) a first charged barrier separating said suppressor bed from said electrode chamber, said first barrier preventing significant liquid flow but permitting transport of ions only of the same charge as said suppressor bed resin exchangeable ions, and
    (f) a second electrode in electrical communication with said suppressor bed outlet section.

2. The suppressor and eluent generator of claim 1 further comprising:
    (g) bridging ion exchange resin of the same charge as said charged barrier and disposed in a connector chamber providing an intermediate ion path between said charged barrier and said electrode chamber.

3. The suppressor and eluent generator of claim 1 further comprising electrode chamber ion exchange resin disposed in said electrode chamber in contact with said first electrode.

4. The suppressor and eluent generator of claim 1 further comprising:
    (g) a second charged barrier of the same charge as said first charged barrier separating said suppressor bed from said electrode chamber, said second barrier preventing significant liquid flow but permitting transport of ions only of the same charge as said suppressor bed resin exchangeable ions, said first barrier being adjacent said suppressor bed and said second barrier being adjacent said electrode chamber, said first and second barriers defining a fluid chamber, and
    (h) a salt solution of an ion of the same charge as said charged barrier and disposed between said first and second charged barriers.

5. The suppressor and eluent generator of claim 1 in combination with:
    (g) a flow-through separator bed of ion exchange resin having exchangeable ions of opposite charge to the exchangeable ions of said suppressor bed, said separator bed having a sample inlet port and an effluent outlet port, said electrode chamber outlet port being in fluid communication with said separator bed inlet port, said separator bed outlet being in fluid communication with said suppressor bed inlet port.

6. The suppressor and eluent generator combination of claim 5 further comprising a detector in fluid communication with said suppressor bed outlet section.

7. The suppressor and eluent generator of claim 1 in which said suppressor bed and eluent generator bed ion exchange resin is a cation exchange resin, said first electrode is a cathode, and said second electrode is an anode.

8. The suppressor and eluent generator of claim 1 in which said suppressor bed and eluent generator bed ion exchange resin is an anion exchange resin, said first electrode is an anode, and said second electrode is a cathode.

9. The suppressor and eluent generator of claim 1 in which said aqueous liquid source comprises a non-recycled independent water source.

10. The suppressor and eluent generator combination of claim 1 further comprising:
    (g) a flow-through detector, and
    (h) a conduit providing fluid communication between the outlet of said flow-through detector and said electrode chamber inlet port.

11. A suppressor and eluent generator for ion chromatography comprising:
   (a) a flow-through suppressor bed of ion exchange resin having exchangeable ions of one charge, positive or negative, having an inlet and an outlet section in fluid communication with fluid inlet and outlet conduits, respectively,
   (b) a first electrode chamber disposed adjacent to said suppressor bed inlet section and having fluid inlet and outlet ports,
   (c) a second electrode chamber disposed adjacent said suppressor bed outlet section and having fluid inlet and outlet ports,
   (d) first and second electrodes disposed in said first and second electrode chambers, respectively,
   (e) a source of flowing aqueous liquid in fluid communication with said first electrode chamber inlet port, and
   (f) first and second charged barriers separating said suppressor bed from said first and second electrode chambers, respectively, said first and second barriers preventing significant liquid flow but permitting transport of ions only of the same charge as said suppressor bed resin exchangeable ions.

12. The suppressor and eluent generator of claim 11 further comprising:
   (g) bridging ion exchange resin of the same charge as said first charged barrier and disposed in a connector chamber providing an intermediate ion path between said first charged barrier and said first electrode chamber.

13. The suppressor and eluent generator of claim 11 further comprising:
   (g) bridging ion exchange resin of the same charge as said second charged barrier and disposed in a connector chamber providing an intermediate ion path between said second charged barrier and said second electrode chamber.

14. The suppressor and eluent generator of claim 11 further comprising first electrode chamber ion exchange resin disposed in said first electrode chamber in contact with said first electrode.

15. The suppressor and eluent generator of claim 11 further comprising:
   (g) a third charged barrier of the same charge as said first charged barrier separating said suppressor bed from said first electrode chamber, said third barrier preventing significant liquid flow but permitting transport of ions only of the same charge as said suppressor bed resin exchangeable ions, said first barrier being adjacent said suppressor bed and said third barrier being adjacent said electrode chamber, said first and second barriers defining a fluid chamber, and
   (i) a salt solution of an ion of the same charge as said charged barrier disposed between said first and second charged barriers.

16. The suppressor and eluent generator of claim 11 in combination with:
   (g) a flow-through separator bed of ion exchange resin having exchangeable ions of opposite charge to the exchangeable ions of said suppressor bed, said separator bed having a sample inlet port and an effluent outlet port, said first electrode chamber outlet port being in fluid communication with said separator bed inlet port, said separator bed outlet being in fluid communication with said suppressor bed inlet port.

17. The suppressor and eluent generator of claim 11 further comprising:
   (h) a third electrode chamber disposed adjacent to said suppressor bed inlet section and having fluid inlet and outlet ports,
   (i) a third electrode disposed in said third electrode chamber,
   (j) a third charged barrier separating said suppressor bed from said third electrode chamber, said third barrier preventing significant liquid flow but permitting transport of ions only of the same charge as said suppressor bed resin exchangeable ions,
   (k) a first fluid conduit between said first electrode chamber outlet port and said third electrode chamber inlet port, and
   (l) a second fluid conduit between said third electrode outlet port and said sample inlet port of the separator bed.

18. The suppressor and eluent generator of claim 11 further comprising a detector having an inlet port and an outlet port, said detector inlet being in fluid communication with said suppressor bed outlet section.

19. The suppressor and generator of claim 18 in which said detector outlet port is in fluid communication with the inlet port of said second electrode chamber, said source of flowing aqueous liquid comprising aqueous liquid flowing out of said detector outlet port.

20. The suppressor and eluent generator of claim 11 in which said second electrode chamber outlet port is in fluid communication with said first electrode chamber inlet port.

21. The suppressor and eluent generator of claim 11 in which said suppressor bed ion exchange resin is a cation exchange resin, said first electrode is a cathode, and said second electrode is an anode.

22. The suppressor of claim 11 in which said suppressor bed ion exchange resin is an anion exchange resin, said first electrode is an anode, and said second electrode is a cathode.

* * * * *